United States Patent
Hatamian et al.

(10) Patent No.: US 11,406,728 B2
(45) Date of Patent: Aug. 9, 2022

(54) SELF-CONTAINED, PORTABLE, SANITIZATION DEVICE AND TELEMEDICINE STATION

(71) Applicant: Vivera Pharmaceuticals Inc., Newport Beach, CA (US)

(72) Inventors: Mehdi Hatamian, Mission Viejo, CA (US); Paul Edalat, Newport Beach, CA (US)

(73) Assignee: Vivera Pharmaceuticals Inc., Newport Beach, CA (US)

( * ) Notice: Subject to any disclaimer, the term of this patent is extended or adjusted under 35 U.S.C. 154(b) by 0 days.

(21) Appl. No.: 17/066,985

(22) Filed: Oct. 9, 2020

(65) Prior Publication Data

US 2022/0111091 A1   Apr. 14, 2022

(51) Int. Cl.
  *A61L 2/18*      (2006.01)
  *A61L 2/24*      (2006.01)
  *A61L 2/28*      (2006.01)

(52) U.S. Cl.
  CPC ............ *A61L 2/18* (2013.01); *A61L 2/24* (2013.01); *A61L 2/28* (2013.01); *A61L 2202/14* (2013.01); *A61L 2202/15* (2013.01)

(58) Field of Classification Search
  CPC ..... A61L 2/18; A61L 2/28; A61L 2/24; A61L 2202/14; A61L 2202/15
  See application file for complete search history.

(56) References Cited

U.S. PATENT DOCUMENTS

| | | | |
|---|---|---|---|
| 3,261,050 A * | 7/1966 | Caille ................... | A47L 23/263 15/301 |
| 10,086,098 B2 * | 10/2018 | Johnson ................... | A61L 2/24 |
| 2007/0140893 A1 * | 6/2007 | McVey ................... | A61L 2/202 422/3 |
| 2016/0195856 A1 * | 7/2016 | Spero ..................... | G06N 5/046 700/90 |
| 2017/0360977 A1 * | 12/2017 | Stibich ..................... | A61L 2/14 |
| 2019/0167829 A1 * | 6/2019 | Grinstead ................ | A61L 2/22 |
| 2020/0129727 A1 * | 4/2020 | Lazarovich .......... | A61B 5/4812 |

FOREIGN PATENT DOCUMENTS

WO    WO-2019246394 A1 * 12/2019 ............. A61L 2/202

* cited by examiner

*Primary Examiner* — Regina M Yoo
(74) *Attorney, Agent, or Firm* — Genius Patent APC; Bruce Angus Hare

(57) ABSTRACT

A sanitization device and telemedicine station (SDTS) may automatically detect and disinfect users as the users pass through the device. Sanitizing solution may be distributed throughout a disinfecting area within the SDTS such that people, pets, items, and/or other objects are disinfected. The SDTS may collect biometric data such as body temperature. Collected data may be analyzed to identify conditions and/or generate recommendations by matching collected data to various condition profiles. The SDTS may allow telemedicine sessions, where a user may communicate with a practitioner or virtual practitioner.

7 Claims, 13 Drawing Sheets

SELF-CONTAINED, PORTABLE, SANITIZATION DEVICE AND TELEMEDICINE STATION

BACKGROUND

Many businesses or other establishments want to monitor and prevent the spread of viruses among their patrons and/or employees. Establishing and implementing monitoring and prevention strategies is costly, time-consuming, and disruptive.

BRIEF DESCRIPTION OF THE SEVERAL VIEWS OF THE DRAWINGS

The novel features of the disclosure are set forth in the appended claims. However, for purpose of explanation, several embodiments are illustrated in the following drawings.

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide a self-contained, portable, sanitization device and telemedicine station (SDTS). The SDTS may allow users (or "subjects") to pass through the device in order to perform a disinfecting process. The disinfecting process may include spraying the environment within SDTS with a disinfecting solution.

The SDTS may provide measurement and/or evaluation of various user attributes (e.g., temperature, weight, heart rate, blood pressure, etc.). In addition, the SDTS may provide interactive medical evaluation and/or feedback, such as indicating measured values that are outside recommended ranges. Such interactive evaluation and feedback may include communication with a health care practitioner (e.g., a medical doctor (MID), nurse, nurse practitioner, physician's assistant, pharmacist, etc.) via the SDTS.

Figure 1A:
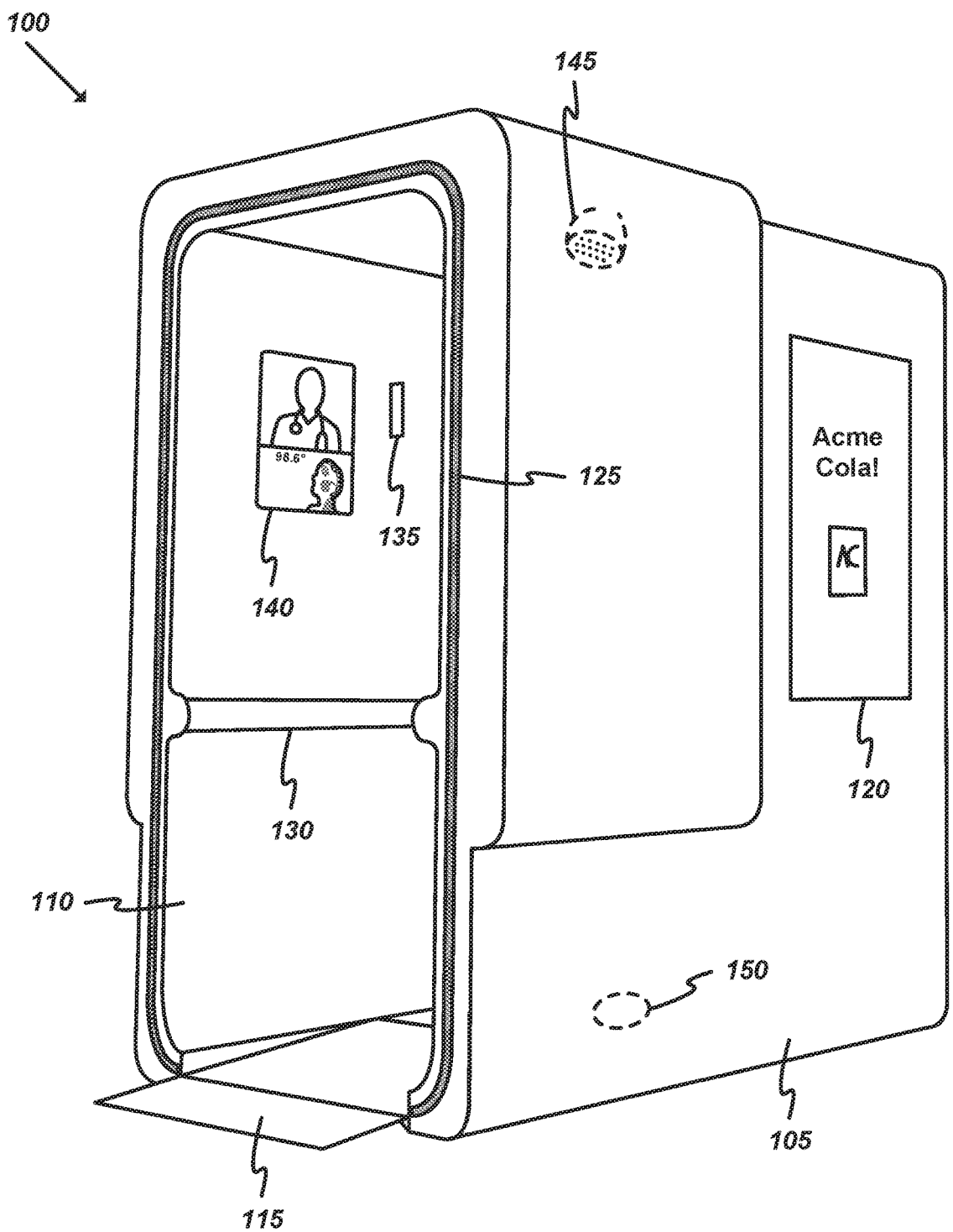
FIG. 1A illustrates a perspective view of a self-contained, portable, sanitization device and telemedicine station (SDTS) according to an exemplary embodiment.

FIG. 1A illustrates a perspective view of SDTS 100 according to an exemplary embodiment. As shown, SDTS 100 may include a housing or outer wall 105, an inner wall 110, a floor 115, a multimedia display 120, various external user interface (UI) elements 125, various internal UI elements 130, various sensors 135, an interactive telemedicine portal 140, a dispenser 145, and a set of fluid control elements 150. SDTS 100 may include various additional electronic and/or electro-mechanical components, such as those described below in reference to FIG. 4.

Returning to FIG. 1A, SDTS 100 may be sized such that users may be able to comfortably walk through the SDTS 100. Such a walk-through configuration helps ensure compliance with sanitization procedures. For instance, in some embodiments, SDTS 100 may be about four feet wide and seven feet tall. Different embodiments of SDTS 100 may be sized differently for differently sized users and/or user types (e.g., children versus adults). SDTS 100 may be deployed at various appropriate buildings, establishments, facilities, areas, etc. Examples of such deployment locations include schools, retail businesses, office buildings, hospitals or other health care facilities, restaurants, places of worship, apartment buildings, and/or any other appropriate location where sanitization and/or telemedicine services may be desired (e.g., parks, private residences, etc.).

Outer wall 105 may include a generally smooth and flat surface that may cover or house various components of SDTS 100, such as structural elements, electronics, etc. Inner wall 110 may include a generally smooth and flat surface that may likewise cover or house various components of SDTS 100.

Floor 115 may include multiple sloped sections (e.g., associated with an entrance and an exit of SDTS 100) and a flat section. The sloped sections may allow access for disabled users. Floor 115 may allow users to walk and stand when interacting with SDTS 100.

Multimedia display 120 may include a display screen, speakers or other audio output elements, and/or other appropriate UI features (e.g., flashing lights or other indicators). Multimedia display 120 may display information related to SDTS 100, such as available services, pricing, etc. Multimedia display 120 may display information related to an establishment or other entity associated with deployment of SDTS 100. Multimedia display 120 may distribute content provided by a network-connected resource, such as a media server. Such a resource may be associated with a venue or establishment, a chain or other association of establishments, and/or other appropriate entities.

For instance, if SDTS 100 is deployed at an entrance to a department store, the store manager may send advertising content, such as a monthly circular or current or future sales event, to SDTS 100 for display by multimedia display 120. Multimedia display 120 may include UI elements such as a touchscreen and/or other input elements (e.g., a microphone for receiving audio commands or data). Multimedia display 120 may include a radio or other wireless communication feature that may allow interaction with user devices such as a smartphone. For example, a user device may be able to send a request for information such as pricing of services, instructions for use, etc., where the requested information may be provided via multimedia display 120 and/or in a response message to a user device.

External UI elements 125 may include features such as a lighted strip or other indicator. For instance, UI element 125 may turn green to indicate that SDTS 100 is available for use and may turn red to indicate that SDTS 100 is not available for use, such as when a previous user has not completely exited SDTS 100. UI elements 125 may further indicate status through use of blinking or flashing lights or colors. For instance, a flashing red light may indicate a temporary delay, such as during an automated SDTS 100 disinfection cycle, while a continuous red light may indicate that SDTS 100 is in use or out of service.

Internal UI elements 130 may include various guides, indicators, physical interaction features, and/or other appropriate elements. For instance, internal UI elements 130 may include a lighted handrail. Different embodiments may include various different internal UI elements 130, such as handles, straps, seats or benches, etc.

In some embodiments, external UI elements 125 and/or internal UI elements 130 may include features for indicating an alarm condition. Such an alarm condition may include a user measurement, such as body temperature, that is outside a specified range. Another example alarm condition includes failure of a facial scan to match a roster of authorized individuals. Such alarm indication features may include lights, sirens, and/or other indications (e.g., by sending an alarm message to an external security system or other resource, such as a user device). In some cases, an alarm condition may be associated with user instructions or indications. For instance, if measured body temperature is above a specified range, UI elements 125 and/or 130 may indicate that a user should wait for further evaluation and/or initiation of treatment protocols (e.g., by flashing a red light).

Sensors 135 may include various biometric sensors, such as a heart rate monitor, blood pressure sensor, temperature sensor, blood oxygen sensor, scale (for measuring bodyweight), height sensor for measuring the height of the subject, glucose meter, etc. Some such sensors may directly perform measurements on a user while others may receive test strips or other collected samples for analysis (e.g., swabs, containers of fluids, etc.). In addition to biometric sensors, sensors 135 may include various types of cameras (e.g., visible light spectrum, infrared (IR), etc.) and/or imaging devices and/or other appropriate sensors, depending on the application environment.

Sensors 135 may include motion detection sensors and/or other sensors that may be able to detect user movements or positions. Such motion detection sensors may be able to detect when a person or object enters and/or exits the SDTS 100.

Motion detection may be utilized to provide a touchless UI in some embodiments. For instance, a user may raise a right hand to request a practitioner. As another example, a user may form an "X" with the arms to terminate a session. In addition, such sensors may be able to determine user position and provide feedback, if needed, such that accurate scanning or measurement may be conducted.

In some embodiments, sensors 135 may include movable, adjustable, or configurable elements. For instance, a camera may be able to move along a vertical axis in order to accommodate users of varying height. As another example, a non-contact forehead thermometer may have an automated aiming feature that is able to receive feedback from a camera and position the thermometer beam for an accurate measurement.

Interactive telemedicine portal 140 may include a display screen, speakers or other audio output devices, a microphone or other audio input device, wireless communication capabilities, and/or other appropriate elements. Telemedicine portal 140 may be associated with various communication features, such as cellular radios, local or distributed network connectivity, etc. that may allow communication with one or more practitioners or other resources.

In some embodiments, telemedicine portal 140 may be associated with a virtual practitioner that may be able to analyze user data and/or generate advice or otherwise interact with a user. For instance, if a user has a measured heart rate that is higher than a specified threshold, the virtual practitioner may indicate the measured value and recommend follow-up with a physician or other practitioner. Such a virtual practitioner may utilize artificial intelligence (AI) and/or machine learning to improve and/or expand analysis and interaction capabilities of the virtual practitioner. For instance, users may provide feedback indicating whether any recommendations were perceived as relevant or beneficial. As another example, the virtual practitioner may recommend diet plans for overweight users and use measured weight loss (as determined by subsequent weight measurements collected by SDTS 100) of those users to update the diet plan recommendations.

In some embodiments, telemedicine portal 140 may allow users to select a virtual practitioner or other interface features. For instance, an SDTS 100 associated with a school may identify individual students via facial recognition and present a virtual practitioner previously associated with the identified user. Thus, for example, each student may be able to select a favorite cartoon character or celebrity with which to interact, thus encouraging use and compliance. SDTS 100 may make a default virtual practitioner selection based on various appropriate factors. For instance, a mascot or spokesman associated with a retail chain may be identified as a default selection for any SDTS 100 associated with the retail chain. As another example, a regional sports star may be selected as a default option based on geographic location of an SDTS 100.

In this example, telemedicine portal 140 includes a split screen display, with a practitioner (or virtual practitioner) in the top portion of the display screen, and a portion of a heat scan of a user in the bottom portion of the display screen. The telemedicine portal 140 display may further indicate measured values, such as temperature, and/or provide other feedback to a user. A practitioner may be provided with a similar split screen interface at a practitioner device such as a smartphone or tablet, and/or otherwise be able to retrieve measured user data and/or interact with a user via SDTS 100.

In some cases, telemedicine portal 140 may provide instructions or other indications in response to detection of an alarm condition or other detected condition. For example, if the measured body temperature of a user is above a threshold, the user may be directed to a specific location for further evaluation or treatment, where such directions may be indicated using a display and/or audio output of the telemedicine portal 140.

Dispenser 145 may include various heads, nozzles, diffusers, and/or other elements for dispensing fluids such as disinfecting solutions. Disinfecting solutions may include an organic sanitization mist that disinfects people, pets, and/or other objects that pass through SDTS 100.

Dispenser 145 may be coupled to various conduits or other supply features. Dispenser 145, and/or any supply features coupled to dispenser 145, may include various storage tanks or reservoirs, vaporizers, atomizers, heaters, etc. that may be utilized to dispense disinfecting solution via dispenser 145. For instance, such a disinfecting solution may be stored in liquid form in a tank. A specified amount of liquid may be released and/or otherwise processed (e.g., by atomizing the liquid) to generate a "fog" of dispersed disinfecting solution in SDTS 100. Some embodiments may include multiple dispensers 145 located throughout SDTS 100. Dispersed disinfecting solution may not only disinfect a user of SDTS 100, but also disinfect any garments, personal items, or other objects within a disinfecting space of SDTS 100.

The disinfecting, or "disinfection", or "sanitizing", or "treatment", or "consultation" space or area of SDTS 100 may include an area roughly defined by inner wall 110 (including a ceiling or top surface) and floor 115, where a user may interact with SDTS 100 or the elements thereof, such as telemedicine portal 140.

Some embodiments of SDTS 100 may include or provide specific sanitization and/or sterilization features. For instance, some embodiments may include one or more induction sterilizers. In some cases, SDTS 100 may include an automatic induction hand sterilizer.

Fluid control elements 150 may include, and/or be coupled to, various fans, conduits, dispensers, diffusers, and/or other appropriate elements that may be able to manipulate fluids such as air and fine liquids or mists. In some embodiments, elements such as fans or other flow control elements or features (e.g., blowers, vacuums, compressed air, etc.) may be provided by an external resource that may be connected to a coupling of SDTS 100. Fluid control elements 150 may retain dispensed disinfecting solution within the disinfecting space of SDTS 100. Such an approach may allow touchless use of SDTS 100, by eliminating a need for doors, panels, strips, and/or other barriers. Fluid control elements 150 may evenly distribute fluids within the disinfecting space of SDTS 100.

Each fluid control element 150 may distribute released sanitizing mist (and/or other fluids) throughout the disinfecting space, prevent the distributed mist from exiting the disinfecting space, and collect used fluid from the disinfecting space. One or more fluid control elements 150 may be located at or near the center of the floor 115 area associated with the disinfecting space. In some embodiments, fluid control elements may be located near the bases of the side walls of SDTS 100.

Fluid control elements 150 may be activated (or speed increased) after sanitizing mist is dispensed, such that sanitizing fluid is directed downwards over the body of a user and the used or contaminated mist may be prevented from escaping SDTS 100. Fluid control elements 150 may include, utilize, and/or be associated with, heaters, coolers, dehumidifiers, and/or other environmental adjustment features.

The fluid control elements 150 may be associated with various sensors that may detect air flow, moisture content, and/or other attributes that may be used to at least partly control operations of the fluid control elements 150. For instance, fan speed may be increased if moisture detected at an outer boundary of the disinfecting space exceeds a specified threshold. As another example, fluid control elements 150 may be activated when moisture associated with the sanitizing mist exceeds a threshold associated with one or more sensors associated with dispenser 145, one or more sensors associated with fluid control elements 150, and/or other appropriate sensors.

Different embodiments may include different numbers, arrangements, and/or configurations of fluid control elements 150. For instance, some embodiments may include a circular array of fluid control elements 150 located about a center of the floor 115 of the disinfecting area. Such fluid control elements 150 may have varying shape, as appropriate (e.g., curved elements may be able to provide a circular ring around the standing area of a typical user). Some embodiments of SDTS 100 may include a matrix of many fluid control elements 150 (e.g., tens, hundreds, thousands, or more of such elements).

Each fluid control element 150 that may be individually controlled based on feedback from various sensors of SDTS 100. For instance, some embodiments of SDTS 100 may include pressure sensors or air flow sensors arranged about the entrance and/or exit of the SDTS 100. Based on feedback from such sensors, one or more fluid control elements 150 may be activated, deactivated, and/or otherwise controlled (e.g., by increasing or decreasing air flow through the fluid control element 150). In some embodiments, fluid control elements 150 may include, or be associated with, motion control features, such as actuators, motors, etc. that may allow each fluid control element 150 to be individually positioned or otherwise manipulated via various moveable elements of the fluid control element 150. Such moveable elements may include, for instance, various mechanical couplings associated with one or more axis of movement, and/or combinations thereof.

SDTS 100 may include various hatches, doors, removable outer panels, and/or other features that may allow access to various cavities, storage areas, and/or mechanical interfaces of SDTS 100. Such access features may be located along portions of the inner wall 110 and/or outer wall 105. For instance, storage tanks and conduit associated with sanitizing solution may be located in a cavity between inner wall 110 and outer wall 105 that is accessible through a door or hatch. As another example, such storage tanks may be refillable via a connector of the SDTS 100, where the connector may be accessible via a removable panel.

Further, areas or cavities between the inner wall 110 and outer wall 105 may house or otherwise provide storage for items such as collected samples, supplies such as test strips, medications, etc. Structural elements, such as a frame or other supports may be housed within such cavities. Some embodiments of SDTS 100 may include mechanical features such as actuators, motors, etc., where such features, and associated power and/or control modules may be at least partly housed by the storage cavities between the inner wall 110 and outer wall 105.

Figure 1B:
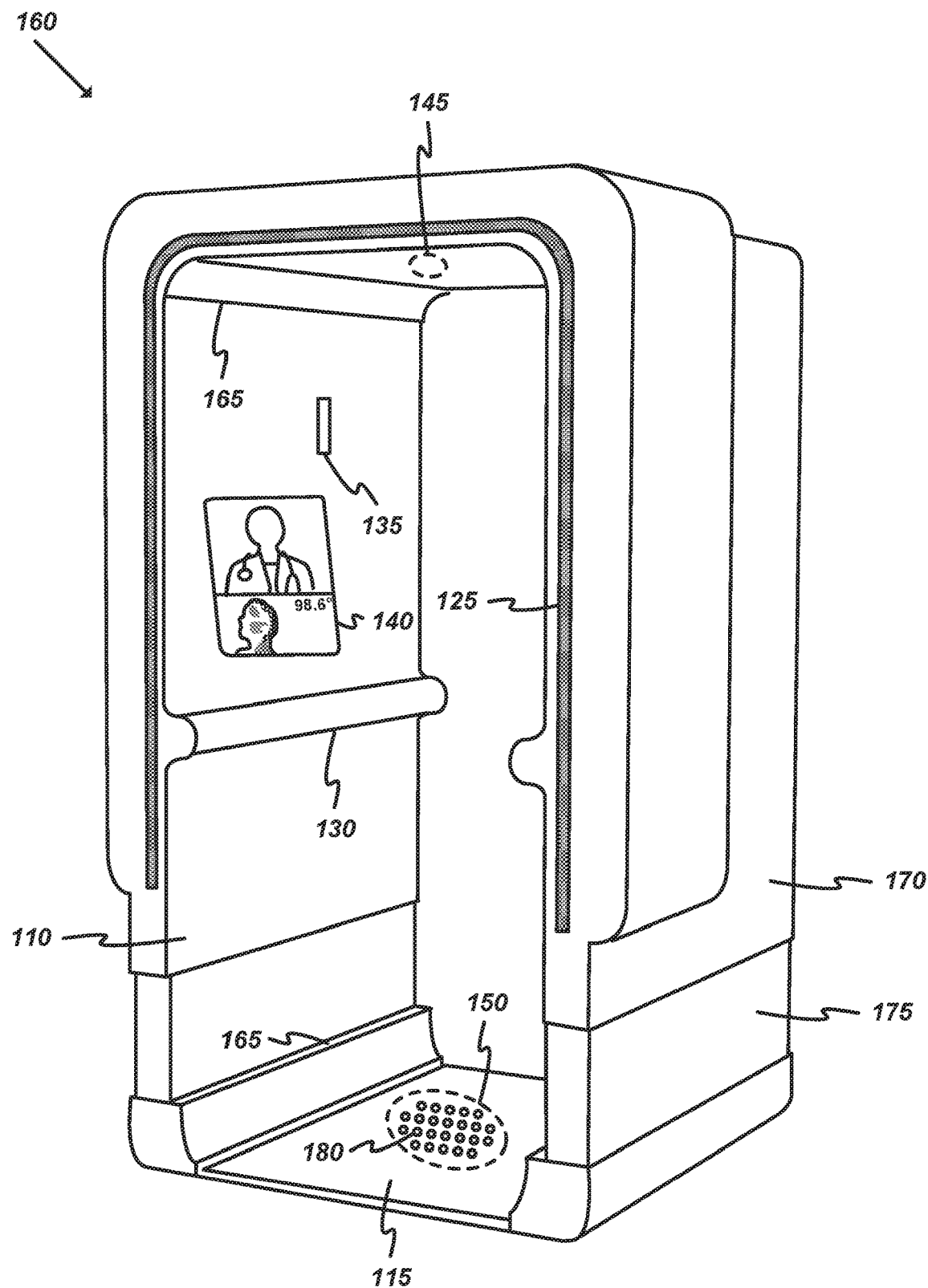
FIG. 1B illustrates a perspective view of an alternative SDTS according to an exemplary embodiment.

FIG. 1B illustrates a perspective view of an alternative SDTS 160 according to an exemplary embodiment. SDTS 160 may include any of the features discussed in reference to SDTS 100. Likewise, SDTS 100 may include any of the features discussed in reference to SDTS 160. In this example, SDTS 160 may include various UI elements, guides, or lights 165 that are able to indicate status, direct user interactions, generate appropriate lighting or other environmental conditions for capture of image or other data, and/or otherwise able to facilitate user interactions.

As shown, SDTS 160 may include an upper portion 170 and a lower portion 175 that provide height adjustment capability for SDTS 160 such that SDTS 160 may be able to fit through doorways or meet other height requirements associated with various applications (e.g., child-users versus adult-users). Such a height adjustment feature may be associated with various UI elements, such as joysticks, buttons, switches, etc. and/or may be manipulate using UI features of portal 140 and/or other UI features of SDTS 160. The height adjustment feature may include actuators, motors, and/or other such features that may be able to position the upper portion 170 relative to the lower portion 175 in order to adjust the height of the SDTS 160.

Some embodiments of SDTS 160 may include adjustment capabilities related to width and/or depth of SDTS 160. Such dimensional adjustment features may include various hinges, sleeves, columns, collapsible sections, portions, and/or other appropriate features that may allow the dimensions of SDTS 160 to be adjusted.

In this example, SDTS 160 includes a shallow, flat floor 115 that allows access and use of SDTS 160 without any ramps or steps, such as wheelchair access. The floor 115 may include slight tapers at the entrance and exit, and/or other features to facilitate or improve use of and/or access to SDTS 160. Because the shallow floor 115 of SDTS 160 may not allow space for fans, blowers, or fluid control elements 150, floor 115 may include a set of channels or other conduits that are able to intake fluids through a set of holes 180. Different embodiments may include various different arrangements of fluid intake elements, such as holes 180. For instance, some embodiments may include intake slots or holes along inner wall 110, such as near floor 115. Each fluid control element 150 may include various intake features (e.g., holes 180, slots, etc.), flow control elements (e.g., fans, blowers, etc.), and/or conduits or fluid channels that couple the intake features to the flow control elements. Flow control elements (and/or other elements associated with fluid control elements 150) may be located within various wall cavities or other spaces of SDTS 160, as appropriate, such that a flat floor of minimal height may be provided.

Figure 2:
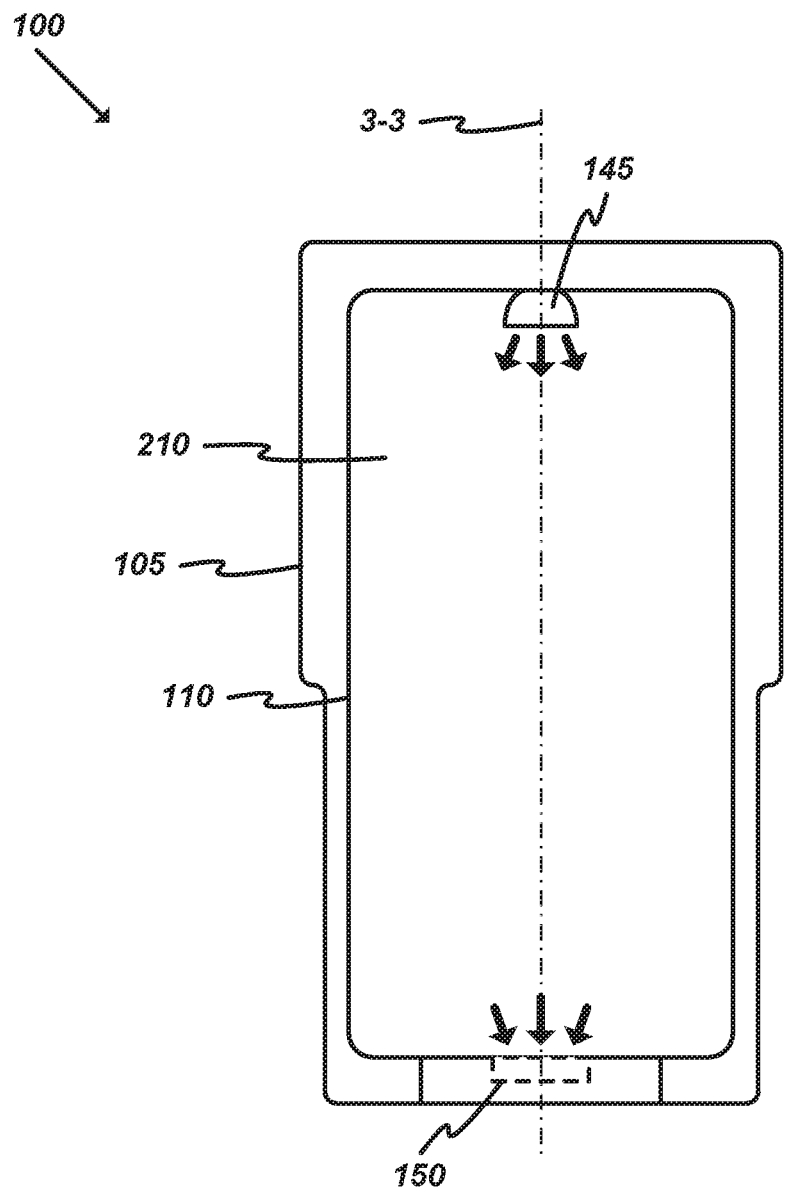
FIG. 2 illustrates a front elevation view of the SDTS of FIG. 1A.

FIG. 2 illustrates a front elevation view of the SDTS 100. SDTS 160, and/or other embodiments of the SDTS, may include similar features. As shown, disinfecting space 210 may include an entrance (e.g., the near opening in this view) and an exit (e.g., the far opening in this view) such that a user may pass through SDTS 100. Some embodiments of SDTS 100 allow multi-directional travel (e.g., in addition to entering through the entrance and leaving through the exit, users may enter through the nominal exit and leave through the nominal entrance). As shown in blown up view 220, each fluid control element 150 may include a curved output and located at each corner of the entrance to disinfection, treatment, and/or consultation space 210. The output flow of each fluid control element 150 may be generally directed toward the center of the entrance to space 210.

Figure 3:
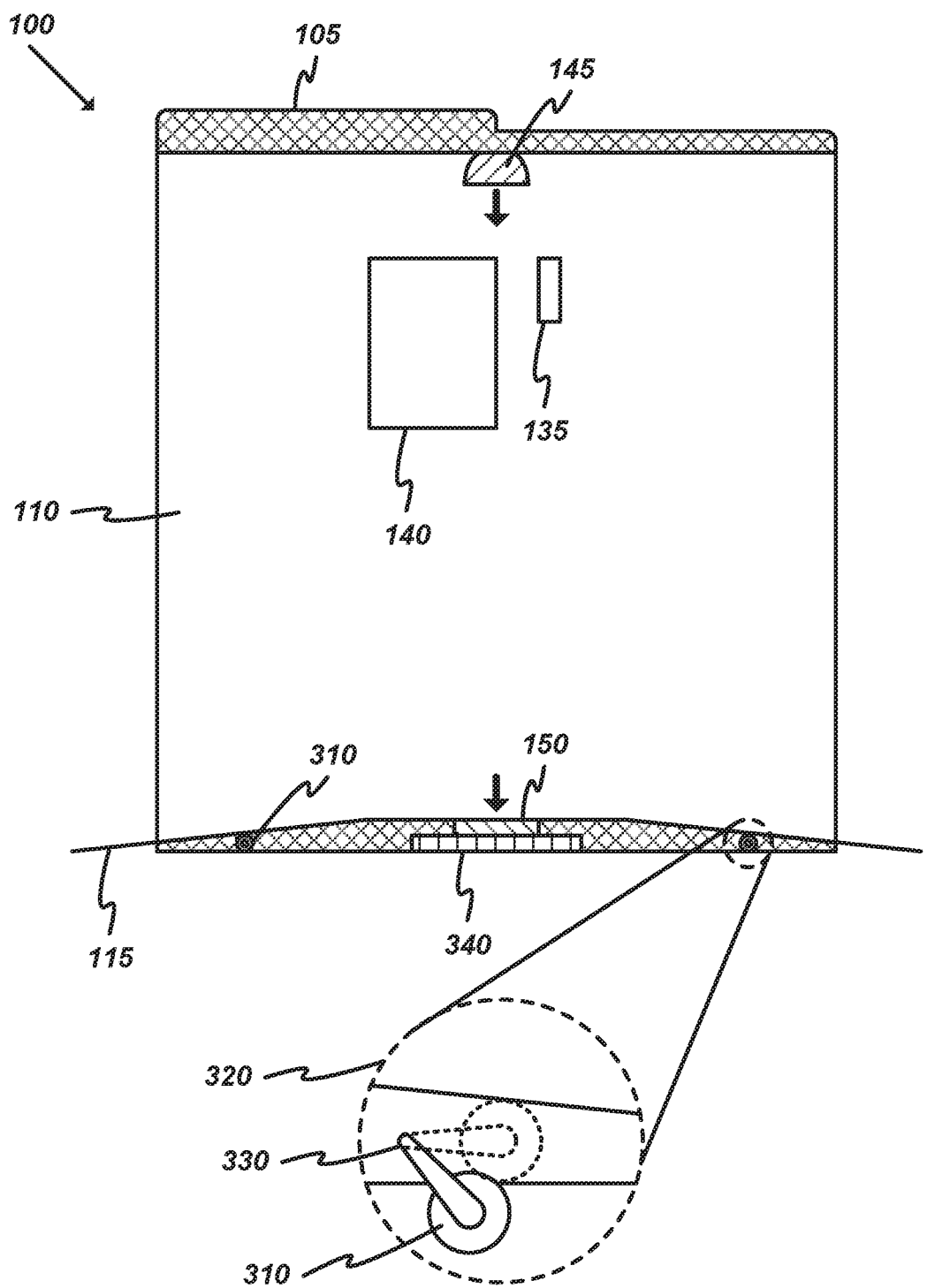
FIG. 3 illustrates a sectional right-side view of the SDTS of FIG. 1A.

FIG. 3 illustrates a sectional right-side view of the SDTS 100 along line 3-3. SDTS 160, and/or other embodiments of the SDTS, may include similar features. In this view, the entrance may be to the left and the exit to the right. In this example, the areas with a crosshatch fill may include various structural elements, storage cavities, electronic and/or mechanical components, conduits, and/or other appropriate elements.

Some embodiments of SDTS 100 may include a set of wheels 310. Such sets of wheels 310 may include various numbers of wheels 310 (e.g., four, six, eight, etc.), where two or more wheels 310 from among the set of wheels 310 may be able to spin or rotate about an axis parallel to line 3-3 such that SDTS 100 may be positioned or steered. As shown in this example, wheels 310 may be housed within an area beneath floor 115 and may be extendable and retractable such that the wheels may be engaged in order to move SDTS 100 and disengaged in order to keep SDTS 100 stationary. Some embodiments of SDTS 100 may include extendable supports or stabilizers that may be used to level, secure, or otherwise position SDTS 100.

As shown in blown up view 320, each wheel 310 may be coupled to an actuator arm 330 such that the wheels 310 may be automatically extended and retracted. Different embodiments may include different mechanical and/or structural features associated with such automatically manipulated wheels 310. Some embodiments of SDTS 100 may include a pushbutton or other appropriate feature for controlling the extension and/or retraction of wheels 310.

Some embodiments of SDTS 100 may include a collection cavity 340. Such a cavity may include a sponge or other such item or material that may absorb fluids. Some embodiments may include outlets or exist nozzles which may be connected to a drain or collection resource. Some embodiments may include heaters or other elements that may remove any moisture from the collected air and disperse only dry, sanitized air.

One of ordinary skill in the art will understand that SDTS 100 may have various other elements and features than those shown. For instance, SDTS 100 may include a frame or other structural support elements or connectors. Such structural elements may include, for instance, beams, columns, rods, struts, ties, etc. Connectors may include, for instance, bolts, screws, pins, welded joints, etc. Some structural elements and/or connectors (and/or combinations thereof) may be formed, machined, and/or otherwise fabricated as integrated units. Structural elements and connectors may include various rigid or semi-rigid materials, such as metal, plastic, wood, etc. As another example, some embodiments of SDTS 100 may include multiple disinfecting or consultation spaces. As still another example, SDTS 100 may include a storage and dispensing feature that may be able to provide supplies or medications, sample collection elements such as test strips, and/or other appropriate objects or items. As another example, SDTS 100 may include, or be associated with, a sun canopy or other light blocking element that may allow for a controlled sensing environment.

Figure 4:
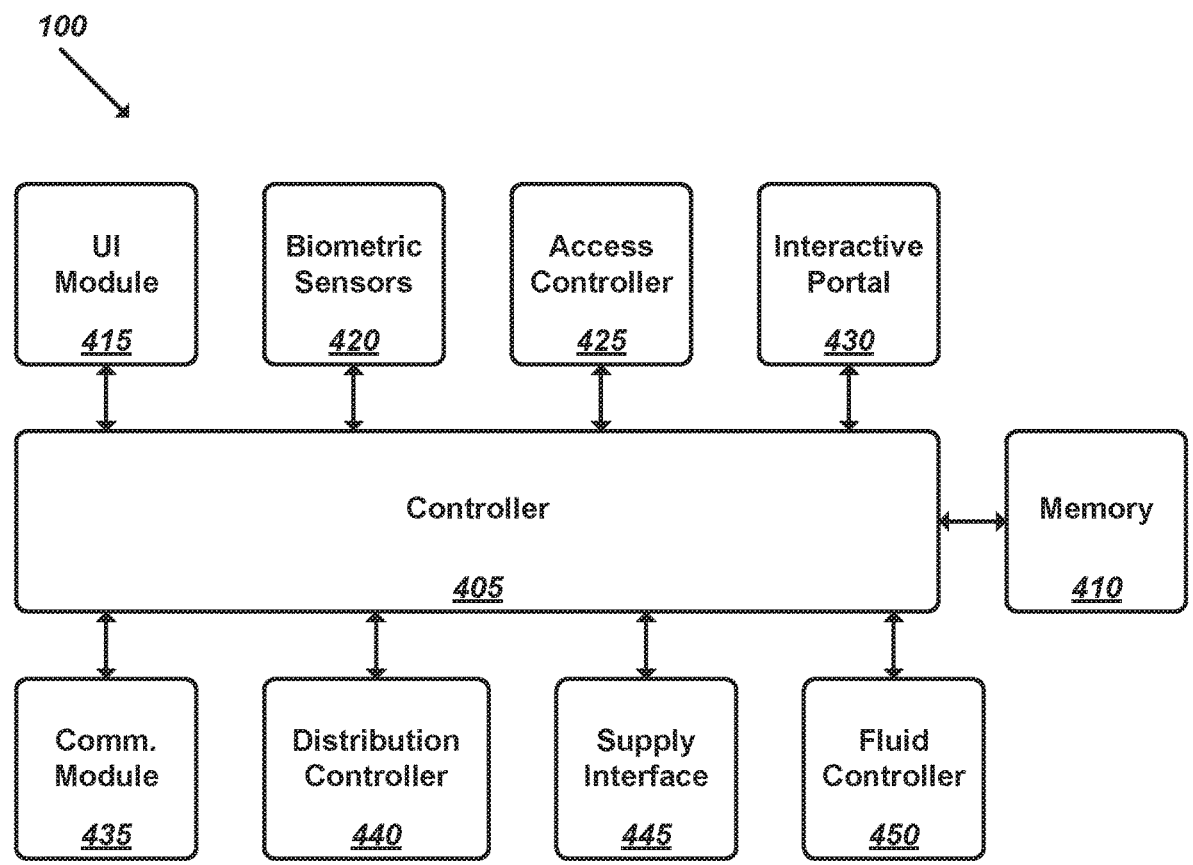
FIG. 4 illustrates a schematic block diagram of the SDTS of FIG. 1A.

FIG. 4 illustrates a schematic block diagram of the SDTS 100. SDTS 160, and/or other embodiments of the SDTS, may include similar features. As shown, SDTS 100 may include a controller 405, a memory 410, a UI module 415, various biometric sensors 420, an access controller 425, an interactive portal 430, a communication module 435, a distribution controller 440, a supply interface 445, and a fluid controller 450.

Controller 405 may include one or more processors, microcontrollers, and/or other elements capable of executing instructions and/or otherwise processing data. Memory 410 may include local and/or network-accessible storage associated with SDTS 100 operating instructions and/or data.

UI module 415 may include, be associated with, and/or otherwise interface to various UI features, such as lighted indicators, audio output devices, display screens, input devices, and/or other appropriate UI elements. In some embodiments, a linked user device such as a smartphone may provide various UI elements.

Biometric sensors 420 may include, for example, temperature sensors, heart rate monitors, blood pressure sensors, pulse oximeters, scales, and/or other appropriate sensors. Biometric sensors 420 may further include devices such as microphones or other audio sensing devices, cameras, etc. that may be able to sense various user attributes (e.g., sounds made by the heart, lungs, or intestines, blood flow, posture, complexion, eye color, etc.). Biometric sensors 420 may generally be touchless or non-contact, but may also include some sensors that contact users, as appropriate (e.g., a pulse oximeter). Such contact sensors, and/or other contact elements of SDTS 100 such as a touchscreen or keypad, may be automatically disinfected by SDTS 100 after use, such as by initiating a disinfecting cycle after a user of a contact sensor is determined to have left SDTS 100.

Some embodiments may include visual aids or references that may be used to determine user information based on captured image data. For instance, a camera may capture an image of the top of a user's head and a reference mark indicating a specified height (e.g., seven feet) and the height of the user may be determined by analyzing the captured image to determine user height based on the reference mark.

Biometric sensors 420 may include one or more cameras of varying type. For instance, some embodiments may include at least one dynamic high-definition (HD) camera that may be used to capture facial photos for recognition analysis. Some embodiments of SDTS 100 may include a large number of such cameras that may be arranged in a matrix distributed about SDTS 100.

In some embodiments, biometric sensors 420 may include at least one precision non-contact human body temperature monitor. Such a temperature monitor may be calibrated and/or tuned for various specific applications. Such "in living body" IR recognition may provide temperature information for one or more areas of the body, as depicted, for example, in the user representation in interactive telemedicine portal 140 of FIG. 1A or FIG. 1B, where the differently shaded areas represent different colors associated with different temperatures.

Returning to FIG. 4, in addition to, or in place of, biometric sensors 420, some embodiments of SDTS 100 may include various other types of sensors. For instance, some embodiments of SDTS 100 may include motion detectors or other sensors that may be able to detect entrance and exit of users and/or objects. As another example, some embodiments may include environmental sensors (e.g., external or environmental thermometers, hygrometers, manometers, etc.) that may be used to normalize biometric measurements and/or control the environment within SDTS 100.

Access controller 425 provide access control through, or with, various features of SDTS 100. Such access control may be associated with specific-user access (e.g., only employees of a business may be allowed access to certain areas via SDTS 100) and/or generic-user access (e.g., only people with a temperature below a specified threshold will be allowed access via SDTS 100. Access control may be associated with data retrieved from various sensors. For instance, one or more cameras of SDTS 100 may be used to capture image data that may be utilized for facial recognition analysis. Some embodiments of SDTS 100 may be able to maintain a local roster of faces (e.g., twenty thousand instances of such reference data) and associated access privileges. Some embodiments of SDTS 100 may include radio frequency identifier (RFID) scanners (and/or other appropriate scanners) for reading user identification information, such as included in a badge with an RFID tag (and/or other appropriate uniquely identifiable devices or items that may be associated with a user and worn or carried, such as a smartwatch or smartphone). Such scanners may be utilized for user detection, identification, and/or access control. Some embodiments of access controller 425 may provide prosthesis attack detection through facial recognition analysis. In some embodiments, facial recognition sensors and/or algorithms may be used to determine whether a user is wearing a mask, where such mask wearing may be a condition for access in some cases.

Access controller 425 may be associated with various relays, actuators, and/or other electro-mechanical features or interfaces of SDTS 100. Such features may be associated with one or more doorways, gates, barriers, etc. that may be used to prevent or otherwise control access via SDTS 100. Access controller 425 may be associated with various UI features of SDTS 100, such as speakers, displays, alarms, etc. that may perform access control by directing users or others (e.g., security personnel) that access is allowed or denied. For instance, if a measured temperature of a user is above a specified threshold, SDTS 100 may provide an audio indication such as a buzzing sound, flash a red indicator light, and/or otherwise provide instructions to a user (e.g., via a display screen) indicating that access is denied due to high temperature.

In some embodiments, access controller 425 may send private messages to one or more users based on measured data in order to protect user privacy. For instance, a user with a higher than allowed temperature may pass through SDTS 100 and then an alert message may be generated and sent to a user device associated with the user, where the alert message may indicate the measured temperature, provide recommended actions, and/or otherwise instruct the user. Likewise, such alert messages may be privately sent to other personnel or entities (e.g., other SDTS 100 devices associated with a facility or an independent security or access control system).

Interactive portal 430 may include a camera, display screen, microphone, speakers, and/or other appropriate UI elements to allow interaction between a user and a practitioner or between a user and SDTS 100. Interactive portal 430 may include, utilize, and/or interact with components such as telemedicine portal 140 and/or sensors 135. Interactive portal 430 may include a virtual practitioner or assistant, and/or other AI features that may be able to analyze collected data, provide feedback to a user, and/or otherwise interact with a user. In some embodiments, interactive portal 430 may be associated with a library of content, such as multimedia presentations or instructional videos that may be identified and/or provided based on measured data and/or user interaction. Such AI features may utilize machine learning to improve recommendations and/or selections based on user feedback.

Interactive portal 430 may provide two-way audiovisual communication between a user and a practitioner. Interactive portal 430 may include, or utilize, a cellular radio, voice over internet protocol (VoIP), and/or other appropriate communication channels.

Interactive portal 430 may provide instructions and/or feedback to a user. For instance, during or prior to disinfection, interactive portal 430 may instruct a user where to stand and provide feedback if a sensed location is not appropriate or correct. As another example, interactive portal 430 may indicate when a disinfection cycle has completed and that a user may exit SDTS 100.

Interactive portal 430 may respond to specific user requests or queries. For instance, voice commands may be recognized and implemented. As one example, a user may request consultation with a practitioner by saying "practitioner". In response, interactive portal 430 may establish a communication channel with a practitioner.

Communication module 435 may allow interaction with various other devices, including other SDTS 100 devices, across various wired or wireless pathways. For instance, communication module 435 may allow user devices such as smartphones and tablets to interact with SDTS 100. Such user devices may be associated with various different types of users, such as SDTS 100 device administrators, patient or pass-through users, employee users, etc. As another example, communication module 435 may be able to connect to and/or otherwise utilize various local and/or distributed networks, such as cellular networks, Wi-Fi networks, Ethernet, etc. in order to communicate with various devices, such as servers, storages, etc. Communication module 435 may include various electro-mechanical interfaces, such as relay interfaces, actuator interfaces, etc. Communication module 435 may include various physical connectors or interfaces, such as universal serial bus (USB) ports, Ethernet ports, etc.

Distribution controller 440 may control distribution of sanitizing mist. Such distribution control may include providing a specified amount of sanitizing mist for a specified duration. Distribution controller 440 may be associated with various distribution elements or dispensers 145. Distribution controller 440 may interact with various atomizers, vaporizers, heaters, diffusers, and/or other elements to generate a sanitizing mist from a liquid sanitizing solution.

In some embodiments, distribution controller 440, or a similar component, may control distribution of test strips, medications, and/or other items or objects (e.g., temporary or visitor badges).

Supply interface 445 may manage and/or provide stored supplies, such as sanitizing solution, test strips, etc. For instance, some embodiments of SDTS 100 may include at least two tanks for storing sanitizing solution such that when a first tank is emptied, a second tank may be selected for use. In this way, SDTS 100 may provide continuous use, while allowing for maintenance such as refilling an empty tank. Supply interface 445 may initiate or send various notification messages. For instance, if an empty tank is detected, a notification to refill the tank may be sent to a technician device or other maintenance resource.

In some embodiments, supply interface 445 may validate or authenticate supplied sanitizing solution such that quality control targets are met and that only appropriate substances are dispensed with SDTS 100. Some embodiments may include a physical or mechanical validation feature, such as a proprietary container or connector. In some embodiments, an inert synthetic agent may be included in the sanitizing solution. Supply interface 445 may include a sensor or tester device that is able to detect the presence of the synthetic agent in order to validate a supply.

In some embodiments, SDTS 100 may include various connectors, valves (e.g., a Wiggins valve), etc., that may allow supplies such as sanitizing solution to be refilled. Supply interface 445 may further allow SDTS 100 to couple to and/or manage distribution of other types of supplies, such as water, compressed air, etc.

Fluid controller 450 may include, or be associated with, various elements such as fluid control elements 150, measurement elements (e.g., pressure sensors, humidity sensors, etc.), and/or other appropriate features, such as a compressed air supply line or storage tank. Fluid controller 450 may at least partly control the operation of fluid control elements 150 in order to prevent fluids, such as sanitizing mist, from exiting disinfection area 210 of SDTS 100. Fluid controller 450 may interact with distribution controller 440 and fluid control elements 150 to control the distribution of sanitizing mist within the disinfection area 210, such that the mist is evenly distributed within the sanitizing area 210. Similarly, fluid controller 450 may interact with distribution controller 440 and fluid control elements 150 to control the containment and removal of sanitizing mist and/or other fluids from SDTS 100.

One of ordinary skill in the art will recognize that SDTS 100 may include various other elements than those described above. For instance, SDTS 100 may include a battery or other energy storage elements, a power management module, and/or power generation features such as solar panels. As another example, SDTS 100 may include fire detection and/or suppression systems. As still another example, SDTS 100 may include a printer or other output device for printing instructions, guides, maps, prescriptions, temporary identification, and/or other information or items.

In addition, SDTS 100 may provide other functionality via the elements described above and below. For instance, each SDTS 100 may act as a server or other network node, providing storage, communication, and processing power.

Figure 5:
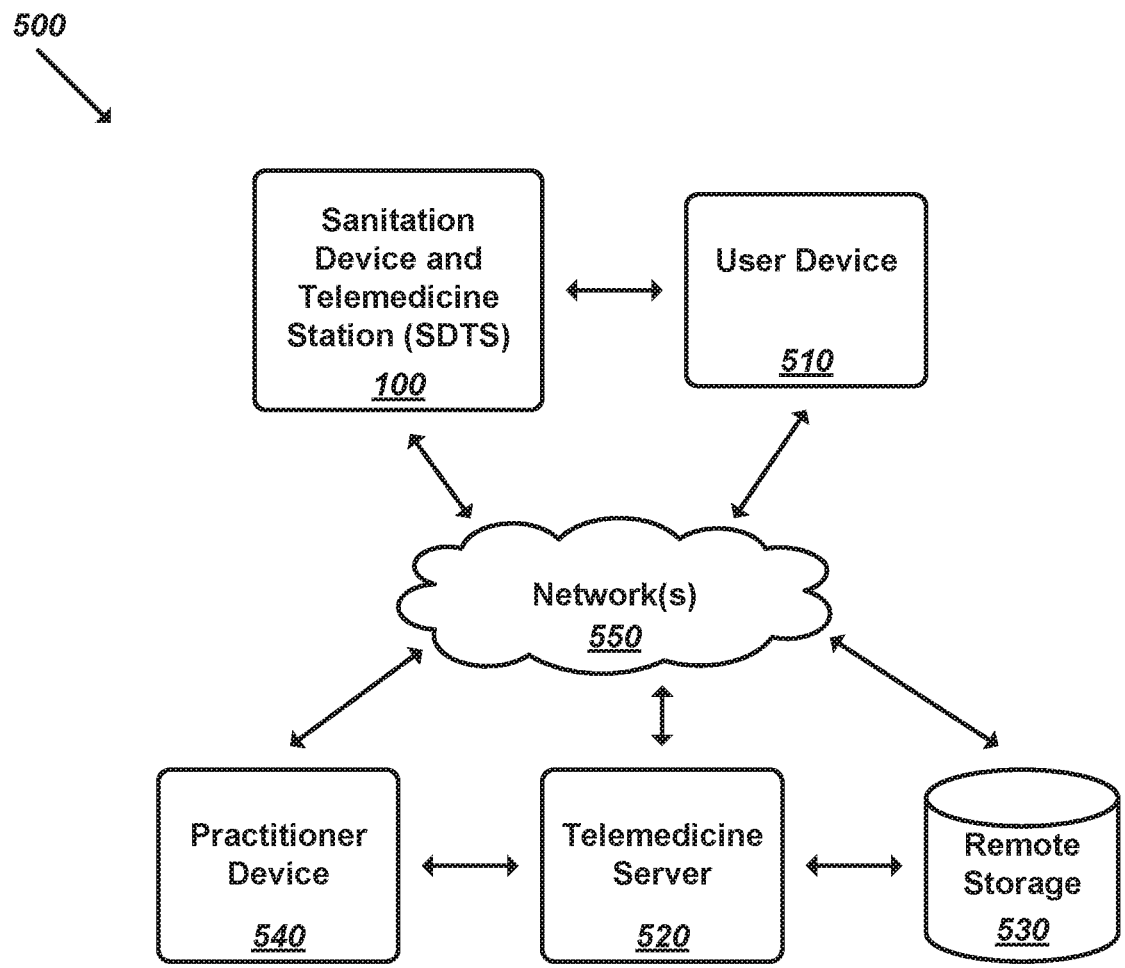
FIG. 5 illustrates an environment in which one or more embodiments of the SDTS of FIG. 1A and/or FIG. 1B may be implemented.

FIG. 5 illustrates an environment 500 in which one or more embodiments of the SDTS 100 may be implemented. As shown, environment 500 may include SDTS 100, one or more user devices 510, a telemedicine server 520, a remote storage 530, one or more practitioner devices 540, and a set of networks 550. SDTS 100 may interact with other components locally, such as via a Bluetooth channel or Wi-Fi link, or via networks 550. In some implementations, SDTS 100 may act as a self-contained, stand-alone device, whereby all data and instructions are stored and/or implemented at SDTS 100 without interaction from other devices.

Each user device 510 may be an electronic device such as a smartphone, tablet, personal computer, etc. that is able to communicate with SDTS 100 locally or via networks 550. Such user devices may be associated with patient-users, administrators, and/or other types of users (e.g., practitioners).

Telemedicine server 520 may be an electronic device that may provide telemedicine resources, such as multimedia presentations, AI algorithms, machine learning models, communication pathways, etc. In some embodiments, an SDTS 100 may serve as telemedicine server 520.

Remote storage 530 may include data and instructions that may be utilized by other components of environment 500. Remote storage 530 may be accessible via an application programming interface (API). Data stored at remote storage 530 may include, for instance, patient or user data (e.g., previous measurements, access dates and times, medical history, etc.), practitioner information (e.g., specialty or practice area, availability, etc.), evaluation criteria (e.g., temperature thresholds, required identification, etc.), and/or other relevant information.

Each practitioner device 540 may be an electronic device such as a smartphone, tablet, personal computer, etc. that is able to communicate with SDTS 100 locally or via networks 550. Practitioner devices 540 may be authenticated or verified in various ways, such as by comparing a device identifier to a list of authorized devices, by comparing practitioner identity information such as a username and password to a list of authorized practitioner-users, and/or other appropriate ways.

SDTSs 100, user devices 510, practitioner devices 540, telemedicine server 520, and/or other associated devices may execute various applications, software, firmware, and/or other sets of instructions stored on computer readable medium that may allow or facilitate communication among the various elements of environment 500.

Networks 550 may include various local and/or distributed networks, such as Wi-Fi networks, Ethernet networks, cellular networks, etc.

Figure 6:
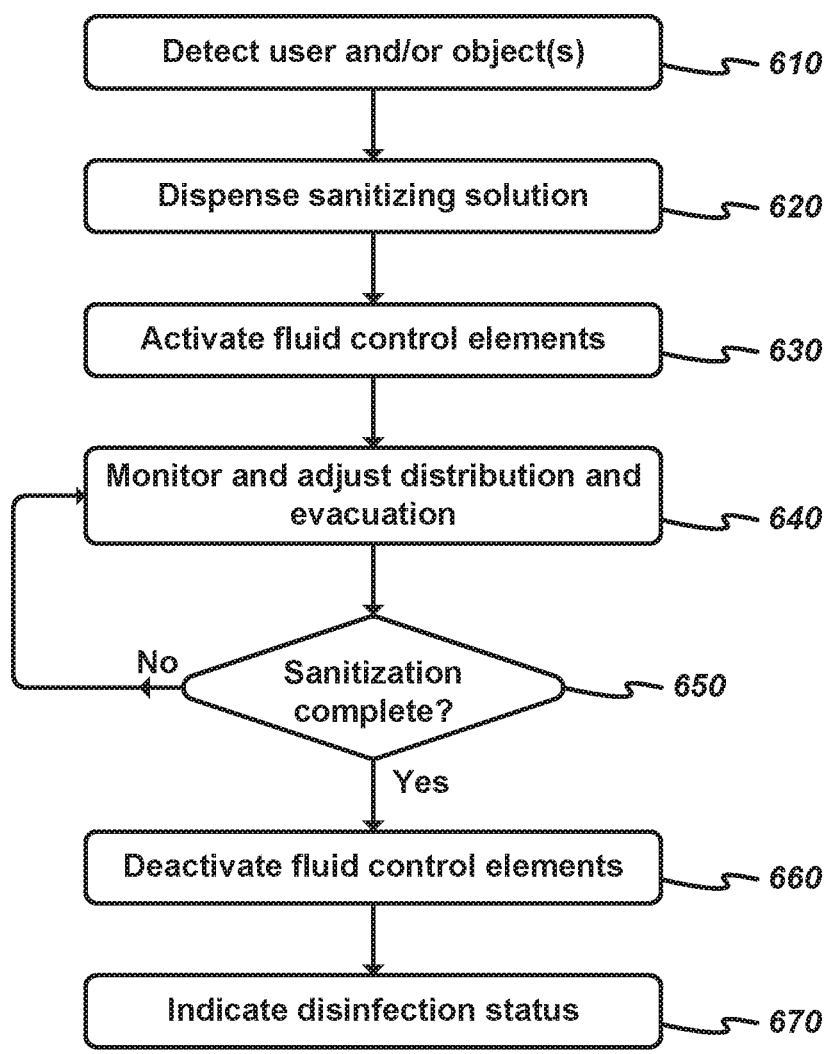
FIG. 6 illustrates a flow chart of an exemplary process that sanitizes people and/or objects.

FIG. 6 illustrates an example process 600 for sanitizing people and objects. People or objects are automatically detected and sanitized in a touchless environment. The process may be performed when a user or object is detected. In some embodiments, process 600 may be performed by SDTS 100.

As shown, process 600 may include detecting (at 610) a user and/or objects at SDTS 100. Such detection may be based on sensed data captured by sensors 420, such as data captured motion detection sensors, cameras, etc. People and/or objects may be detected as they pass through or near an entrance to SDTS 100. If no users or objects are detected, process 600 may continue to monitor the various sensors until a person or object is detected.

The process may include dispensing (at 620) sanitizing solution. Sanitizing solution may be dispensed in specified, measured amounts. Some embodiments may convert liquid solution to a mist or fog that may be evenly distributed throughout disinfecting area 210. Sanitizing solution may be dispensed via a dispenser such as dispenser 145 using various pumps, hoses, fittings, conduit, nozzles, dispensers, etc. In addition to sanitizing solution, some embodiments may utilize ultraviolet (UV) light, heat, ozone, and/or other appropriate sanitizing or disinfecting solutions, compounds, elements, and/or treatments.

Process 600 may include activating or otherwise manipulating (at 630) fluid control elements of SDTS 100. Such elements may be similar to fluid control elements 150 and may distribute sanitizing mist, prevent sanitizing mist from exiting disinfecting area 210, and collect used sanitizing mist. Some embodiments of SDTS 100 may include environmental barriers, such as doors, hatches, flaps, etc. Fluid control elements 150 may be utilized to retain fluids with the disinfecting area 210 such that doors or other physical barriers are not necessary. For instance, one or more fans or blowers associated with fluid control elements 150 may be activated such that fluids are collected via the fluid control elements 150. In addition to activation of fluid control elements 150, SDTS 100 may manipulate fluid control elements 150 by, for instance, increasing or reducing fan speed, adjusting direction or alignment of the elements 150, activating or deactivating some elements 150, etc.

As shown, process 600 may include monitoring and adjusting (at 640) distribution and evacuation of sanitizing mist, as necessary. Various sensors, such as humidity sensors, pressure sensors, etc. may be used to evaluate the distribution of sanitizing solution and/or sense solution near the entrance or exit of SDTS 100. Elements such as dispenser 145 or fluid control elements 150 may be adjusted to improve distribution, containment, and/or removal of sanitizing solution within disinfecting area 210 based on the sensed data. For instance, if a humidity sensor associated with disinfecting area 210 indicates a lower measured humidity than other humidity sensors, a dispenser 145 associated with that area may be activated or its output increased. As another example, fan speed of a fluid control element 150 associated with an area having higher measured humidity may be increased relative to fan speed of a fluid control element 150 associated with an area having a lower measured humidity.

Process 600 may include determining (at 650) whether sanitization is complete. Such a determination may be made based on various relevant factors. For instance, some embodiments of SDTS 100 may dispense a measured amount of sanitizing solution and apply the solution for a specified amount of time. As another example, some embodiments of SDTS 100 may determine whether a threshold humidity or other measure of dispensation (e.g., by using an optical sensor able to detect a relative density of sanitizing fog or mist in the air) of sanitizing solution has been met or exceeded.

The process may include deactivating (at 660) the fluid control elements 150. Such deactivation may include opening any automatic doors, hatches, etc. and/or deactivating dispenser 145 or other dispensation features of SDTS 100. In some embodiments, fluid control elements 150 may be operated at an ambient speed and deactivation may include reducing the speed or volume of the fluid control elements 150 back to the ambient level.

As shown, process 600 may include indicating (at 670) status. For instance, an element such as interactive telemedicine portal 140, UI element 125, and/or UI element 130 may indicate a disinfection status throughout process 600. For instance, interactive telemedicine portal 140 may provide visual or audio status indicators, such as "ready for use", "disinfection in progress", "disinfection complete", etc. As another example, UI element 125 may turn from red to green to indicate SDTS 100 is ready for a next user to enter. As still another example, UI element 130 may turn green to indicate SDTS 100 is ready for use, turn red while in use, and turn blue after disinfection has completed.

Figure 7:
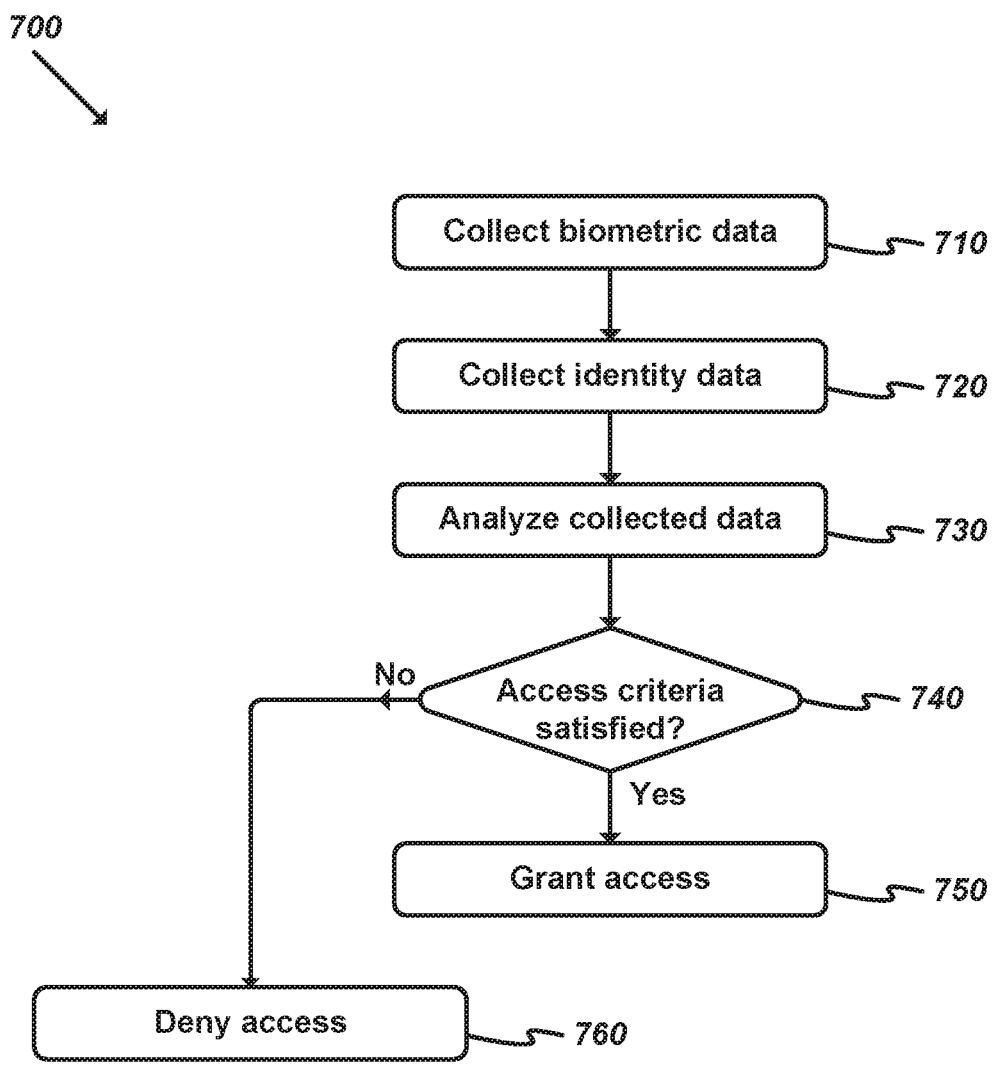
FIG. 7 illustrates a flow chart of an exemplary process that provides access control based on biometric screening data.

FIG. 7 illustrates an example process 700 for providing access control based on biometric screening data. Process 700 may evaluate user identity and/or biometric data to determine whether access to a facility should be granted. The process may be performed when a user is detected. In some embodiments, process 700 may be performed after (and/or at least partially during) process 600. In some embodiments, process 700 may be performed by access controller 425 of SDTS 100.

As shown, process 700 may include collecting (at 710) biometric data. As described above, such biometric data may include body temperature, IR scans, and/or other appropriate data from various appropriate sensors such as sensors 420. In some embodiments, collected data may include user self-evaluation data and/or other user feedback. For instance, a user may be prompted to indicate various attributes, such as amount of pain, energy level, perceived symptoms (e.g., dry throat, itchy eyes, joint pain, etc.).

Process 700 may include collecting (at 720) identity data or other access verification data. Types of data collected may depend on the type of facility, security protocols, and/or other access restriction criteria, if any. SDTS 100 may include various sensors or interfaces for receiving identity information. For instance, SDTS 100 may include an RFID scanner that is able to read employee badges that include RFID tags. As another example, SDTS 100 may include a camera that is able to scan tickets or graphic codes.

In some embodiments, SDTS 100 may utilize facial scanning, facial recognition, and/or other biometric sensed information (e.g., movement patterns captured via a video camera, vocal or other audio information captured via a microphone, heat patterns captured via an IR sensor, etc.) to collect identity data.

The process may include analyzing (at 730) the collected data. Such analysis may include, for instance, processing captured biometric data, such as by filtering, smoothing, and/or other processing captured data. Analysis may include comparison of collected data to various thresholds or other evaluation criteria. For instance, an employee ID number read from an RFID badge tag may be compared to a list or lookup table of active employees or valid ID numbers. As another example, sensed body temperature may be compared to a maximum threshold.

As shown, process 700 may include determining (at 740) whether any specified access criteria have been satisfied. An administrator-user may be able to interact with SDTS 100 to define or set such access criteria or access restriction criteria. In some cases, default or nominal criteria may be utilized if no criteria are specified.

The access restriction criteria may include various thresholds (e.g., maximum temperature, minimum blood oxygen saturation, etc.), boundaries, and/or other comparative limits. In some cases, access restriction criteria may indicate a specific set of authorized users and/or type(s) of users (e.g., employee areas of a business may limit access to certain employees, an entertainment venue may limit access to ticketholders, etc.). Such users may be associated with ID badges, event tickets or other admission credentials, and/or other appropriate documentation. In some embodiments, users may be associated with profiles that may include various types of identifying information (e.g., a reference movement video, a reference facial scan, etc.).

Process 700 may include granting access (at 750) if the process determines (at 740) that the access criteria is satisfied. Such granting of access may include, for instance, providing an indication such as a green light or audio cue ("access granted" or "please proceed") that any specified access criteria have been satisfied. In some embodiments, process 700 may send an access grant message or other appropriate message or signal to one or more electro-mechanical objects or devices associated with access control. For instance, access controller 425 may be associated with a relay or solenoid that controls a gate or door at the exit of SDTS 100. As another example, a grant message may be wirelessly transmitted to a security system or device (e.g., a door with controlled access) associated with the exit of SDTS 100. As still another example, an access grant message may be sent to a user device associated with a security guard or other personnel associated with access control of a facility.

The process may include denying (at 760) access if the process determines (at 740) that the access criteria is not satisfied. Such denial of access may include, for instance, providing an indication such as a red light or audio cue ("access denied") that any specified access criteria have not been satisfied. Similar to above, a denial message may be sent to other resources, such as user devices of security personnel, electro-mechanical objects or devices associated with access control, etc. If access is denied (at 760), various access restriction features may be maintained and/or enabled. For example, a gate or door may be (or remain) locked, closed, and/or otherwise secured.

Figure 8:
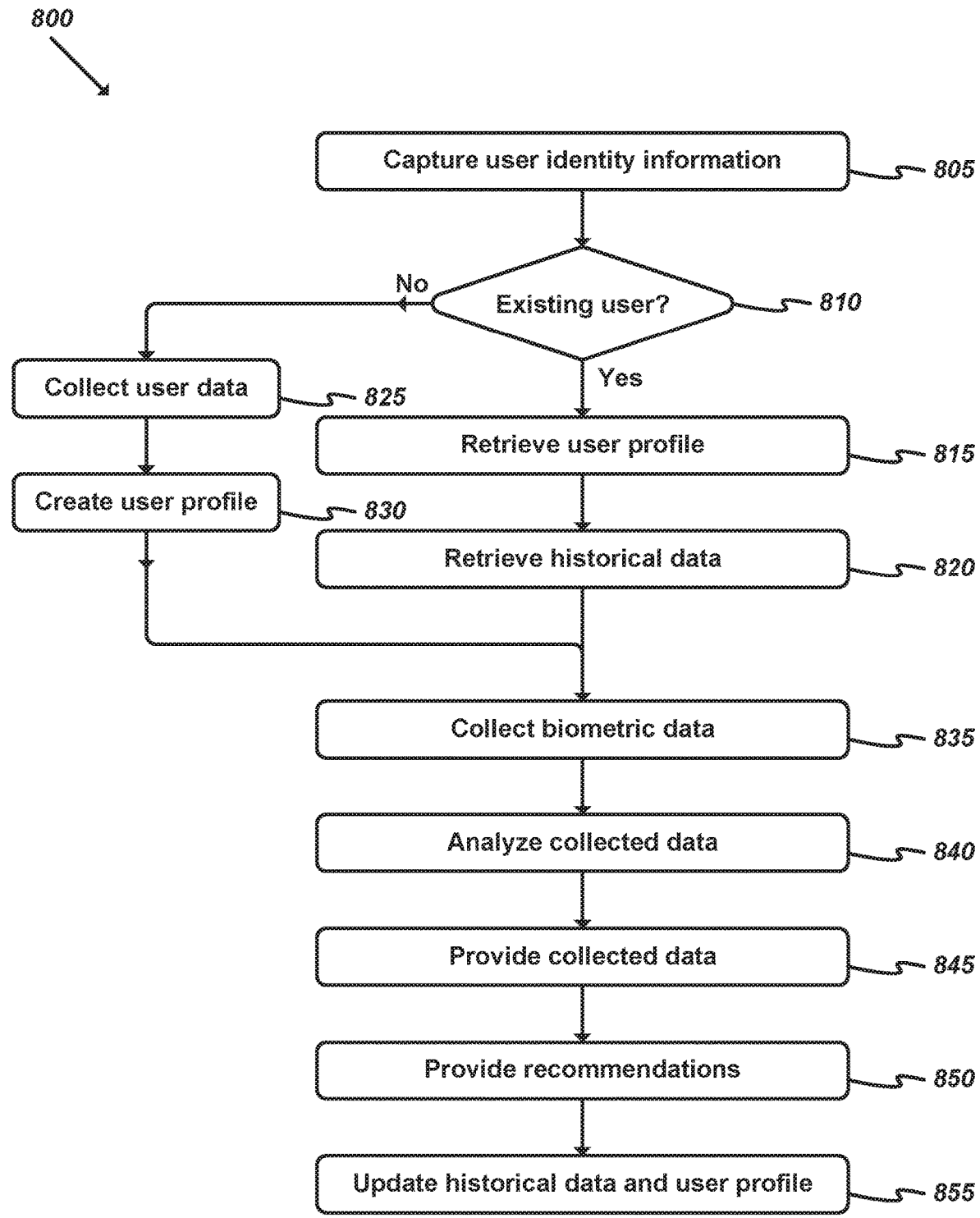
FIG. 8 illustrates a flow chart of an exemplary process that automatically evaluates a user and generates recommendations.

FIG. 8 illustrates an example process 800 for evaluating a user and generating recommendations or otherwise interacting with a user. Such user interaction may include virtual assistance, pre-recorded media or instructions, "live" interactions with a practitioner, and/or other appropriate user interaction. The process may be performed when a user is sensed at an entrance to SDTS 100, when a request for consultation is received (e.g., via telemedicine portal 140), and/or other appropriate circumstances. In some embodiments, process 800 may be performed by SDTS 100.

As shown, process 800 may include capturing (at 805) user identity information. User identity information may include biometric data (e.g., facial photos, movement videos, etc.), biographic data (e.g., name, identification number, etc.), and/or demographic data (e.g., age, ethnicity, gender, etc.). Such information may be captured using various appropriate resources, such as a facial recognition camera or other device, audio input devices, via wireless communication with a user device, and/or other appropriate ways (e.g., via a touchscreen, keyboard, or keypad).

Process 800 may include determining (at 810) whether the user is an existing user. Such a determination may be made in various appropriate ways. For instance, captured facial or movement information may be compared to stored user profiles in order to determine whether a match is able to be identified. As another example, an employee ID number may be compared to a list of employee profiles to determine whether there is a profile associated with the employee ID number. As still another example, communication with a user device such as a smartphone may be established, and user device information may be compared to a listing of known devices.

The process may include retrieving (at 815) a user profile if an existing user is identified (at 810). Such a user profile may be retrieved from a local or remote storage or other resource (e.g., a server, an API, etc.). The user profile may include demographic information, user-specific evaluation criteria, existing or known conditions, associated practitioners, insurance information, user preferences, medications or prescriptions, etc.

As shown, process 800 may include retrieving (at 820) historical data. Such data may be retrieved from a local or remote storage or other resource. Historical data may include, for instance, biometric measurements (e.g., temperature, bodyweight, etc.), virtual or actual practitioner interaction history, grants (and/or denials) of access, and/or other historical data.

Process 800 may include collecting (at 825) user data if an existing user is not identified (at 810). Different embodiments may collect different user data, depending on the application, preferences specified by an administrator-user, and/or other appropriate criteria. User data may include, for instance, demographic information such as name, age, etc., health information such as existing conditions, current medications, etc., insurance information, employment information, and/or other relevant information.

The process may include creating (at 830) a user profile based on the collected information. The user profile may be stored locally at SDTS 100, and/or sent to other resources, such as a server, storage, and/or other SDTSs 100.

As shown, process 800 may include collecting (at 835) biometric data. Such biometric data may be collected using biometric sensors 420. Collected data may include data reported from other sources. For instance, blood glucose measurements may be received from a user device associated with the user, such as via an application of some embodiments running on user device 510. In some cases, data may be received from a practitioner device or may be entered or provided manually at SDTS 100. For instance, a technician may measure user temperature using a handheld device and enter the information into a practitioner device 540 such that the information may be transmitted to SDTS 100.

Collected data may be processed in various appropriate ways. For instance, some values may be calculated or otherwise determined based on measured data. For example, resting heart rate may be estimated based on measured heart rate. As another example, body mass index (BMI) may be calculated based on weight and height measurements.

Process 800 may include analyzing (at 840) the collected data. Such analysis may include comparison to various thresholds or limits, comparisons to model or default data, and/or other analysis. For instance, biometric measurements may be compared to various thresholds and measurements that are outside recommended ranges may be flagged.

Some embodiments may include profiles or models associated with various illnesses, ailments, injuries, and/or other conditions. For instance, a virus may be associated with fever and low blood oxygen saturation levels. As such, a profile associated with the virus may include an upper temperature threshold and a lower blood oxygen saturation threshold. As another example, diabetes may be associated with an upper blood glucose threshold.

Such condition profiles may include sets of biometric measurements and associated thresholds, reference data such as images or video associated with healthy and/or ill subjects, audio data associated with healthy and/or ill subjects, etc. Such profile information may be used to evaluate user complexion, eye color, tongue color, and/or other visual attributes that may be indicative of one or more conditions. Likewise, audio profile information may be used to evaluate breathing, heart function, etc.

Condition profiles may include differential, relative or offset, and/or other types of thresholds or limits. For instance, a significant percentage change in a measured value (e.g., heart rate) from a previous measurement may indicate a condition even if both values are within a recommended or nominal range.

Condition profiles may be updated or modified based on known or previously identified conditions. For instance, a user who is known to suffer from diabetes may be associated with a profile having more restrictive blood glucose limits than an otherwise similar user who is not known to suffer from diabetes.

In some embodiments, nominal or default profiles may be utilized. For instance, if an SDTS 100 is deployed at an elementary school, one or more default profiles specific to the associated age group may be used without regard to identity of individual users.

Some embodiments may use machine learning to generate and/or update condition profiles and/or other models. For instance, user information such as diagnosed illnesses or conditions may be received and analyzed, along with other collected user data, to generate condition profiles or update existing profiles. For example, if a number of users report having cold-like symptoms after SDTS 100 measurements indicating elevated heart rate and a change in complexion color, condition profile selection models may be updated such that future users with those symptoms are identified (and potentially treated, isolated, or otherwise managed) in a timely manner.

The process may include providing (at 845) collected data. Such data may be provided in various appropriate ways. For instance, measured data or captured images or scans may be provided via a resource such as telemedicine portal 140. As another example, a message including the measured data may be sent to an associated user device and/or practitioner device. Collected data may be stored for future use and/or analysis.

As shown, process 800 may include providing (at 850) recommendations. Such recommendations may be generic (e.g., "keep active"), region-specific (e.g., "avoid exposure during noon-time sun"), and/or user-specific (e.g., "elevated heart rate—consult with medical practitioner", "slight fever—maintain distance from others and submit sample for testing", etc.). Recommendations may include progress toward goals (e.g., "five pounds lost in past four weeks, ten pounds remaining to goal"). Recommendations may include recommended actions (e.g., rest, drink fluids, seek medical attention, etc.), recommended tests or evaluations (e.g., comprehensive blood panel, sleep apnea screening, etc.), and/or other appropriate recommendations.

In some embodiments, provided recommendations may be conditional and/or based on user feedback or other relevant factors. For instance, recommendations associated with a fever may include fever-reducing medications. However, if the user (or previously collected user profile information) indicates an allergy to such medications, a modified fever recommendation may exclude such medications and instead recommend a lukewarm bath and rest.

In some embodiments, operations 835-850 may be iterated multiple times. For instance, a first measurement and recommendation may indicate a slight fever. In response, the user may be asked to submit a swab sample for analysis or additional scans or measurements may be performed to corroborate or disprove the original recommendation or indication. For instance, if a temperature sensor indicates a higher body temperature than a specified threshold, a more accurate IR scan may be performed to verify the measurement. As another example, if a user indicates a rash as a symptom through audio feedback, an image of a portion of the affected area may be captured.

Process 800 may include updating (at 855) historical data and the user profile. User profile information and/or historical data may be updated to include any new measurements or other collected data, user feedback, and/or other collected data (e.g., updated user profile information).

Figure 9:
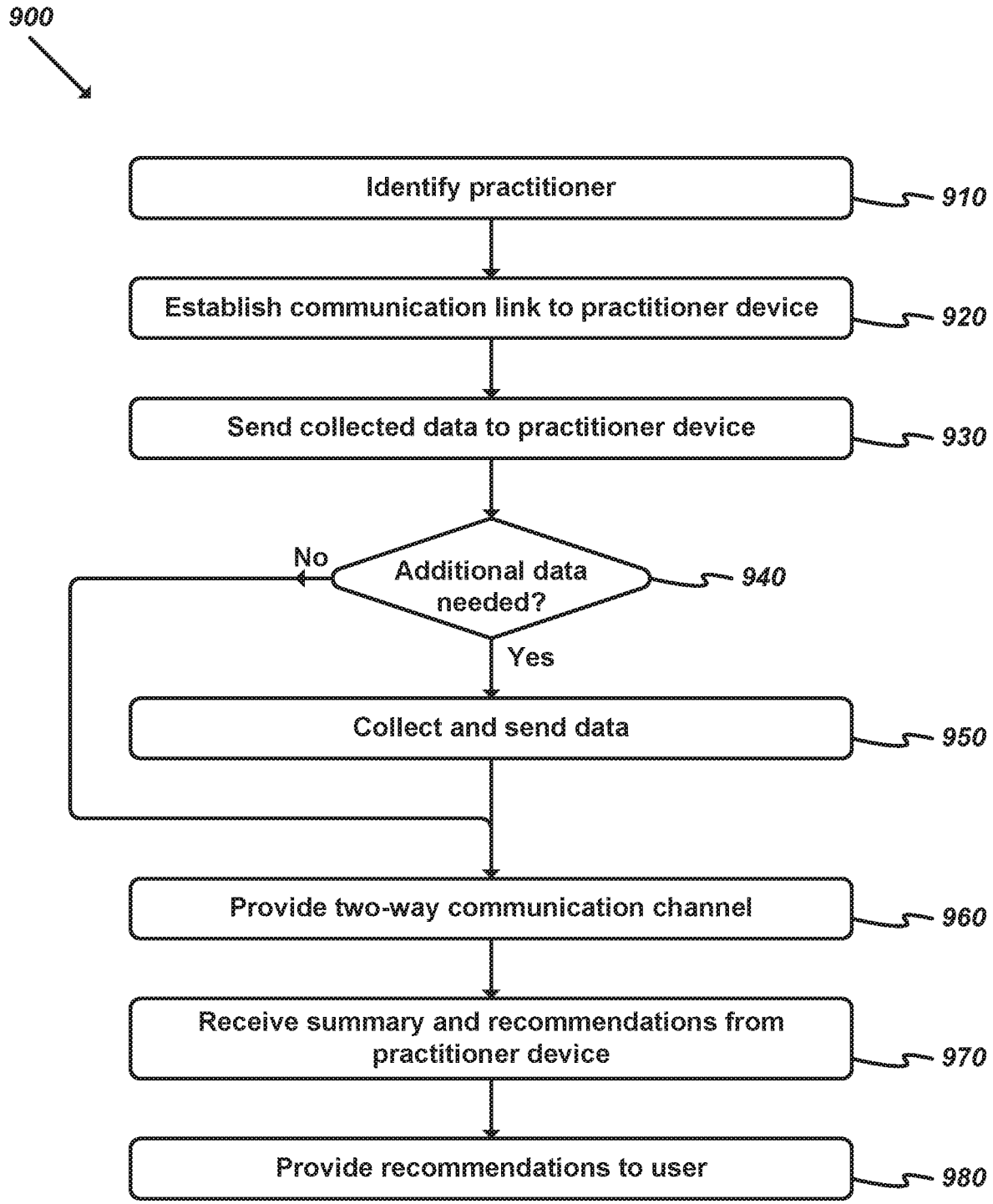
FIG. 9 illustrates a flow chart of an exemplary process that provides telemedicine services.

FIG. 9 illustrates an example process 900 for providing telemedicine services. The process may allow users to receive remote telemedicine services with a practitioner or virtual practitioner. The process may be performed when a user enters SDTS 100, when a user remains or lingers within consultation space 210 for a specified duration, when a request for a conference is received from a user, and/or under other appropriate conditions. In some embodiments, process 900 may be performed by interactive portal 430 of SDTS 100.

As shown, process 900 may include identifying (at 910) a practitioner. Such a practitioner may be identified in various appropriate ways. For instance, a roster of active or available practitioners may be provided to SDTS 100. As another example, a practitioner may be associated with a user profile. In some embodiments, a virtual practitioner may be identified. Such a virtual practitioner may be identified based on a user profile, a site or facility profile, and/or based on other appropriate criteria (e.g., a default selection).

Process 900 may include establishing (at 920) a communication link to a practitioner device. Such a link may utilize various local and/or distributed networks and/or other appropriate channels. If a virtual practitioner is selected, the communication link may be associated with a server device or a local resource. The communication link may include data, audio, video, telephony, and/or other appropriate communication capabilities.

The process may include sending (at 930) collected data from SDTS 100 to the practitioner device. Such data may include measured biometric data, user feedback (e.g., self-evaluation as to pain level, energy level, etc.), and/or other collected data (e.g., images, recorded audio, etc.).

As shown, process 900 may include determining (at 940) whether additional data is needed. Such a determination may be made in various appropriate ways. For instance, the practitioner device may receive a request from the identified practitioner and the request may be forwarded to SDTS 100.

Process 900 may include collecting and sending (at 950) additional data if the process determines (at 940) that additional data is needed. Such additional data may include receiving data from the same sensors multiple or additional times (e.g., multiple successive temperature measurements may be averaged or otherwise filtered to generate a single result). Additional data may further include utilizing additional or different sensors to collect measurements. For instance, an initial scan may use a single camera to capture complexion data. Additional data may then include using multiple of such cameras to capture complexion data. As another example, images may be captured with different types of fill lighting (e.g., white light, blue light, etc.), lighting intensity may be varied, etc.

The process may include providing (at 960) a two-way communication channel between SDTS 100 and a practitioner device, server, virtual practitioner, and/or other appropriate resource. The communication channel may allow audio-visual communication between a user and a practitioner.

As shown, process 900 may include receiving (at 970) a summary and recommendations from the practitioner device or virtual practitioner. Such summary and recommendations may include written notes, prescriptions, referrals, and/or other appropriate recommendations and/or indications, as appropriate.

Process 900 may include providing (at 980) the received recommendations to the user. The summary, recommendations, and/or indications may be provided via SDTS 100, such as via telemedicine portal 140. In some embodiments, SDTS 100 may include a printer or other output device for printing prescriptions or other appropriate documents. The summary, recommendations, and/or indications may be sent to a user device associated with the user and/or otherwise sent to the user (e.g., via email or text message).

Figure 10:
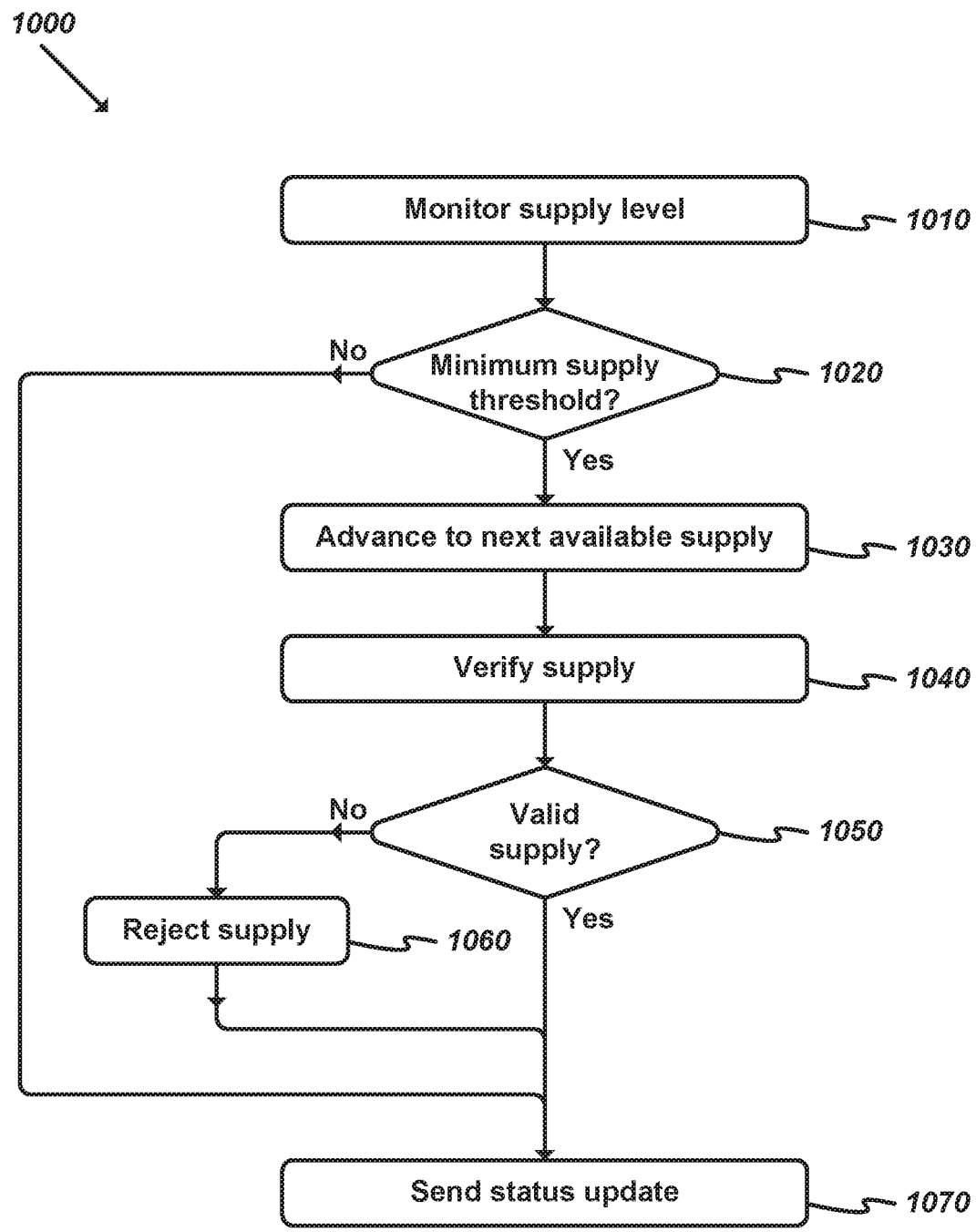
FIG. 10 illustrates a flow chart of an exemplary process that monitors, replenishes, and validates supply of sanitizing solution.

FIG. 10 illustrates an example process 1000 for monitoring, replenishing, and validating a supply of sanitation compounds. Such a process may allow SDTS 100 to operate for longer periods before resupply or other maintenance. The process may be performed whenever a disinfection cycle is completed and/or other appropriate times. In some embodiments, process 1000 may be performed by SDTS 100. Some embodiments of SDTS 100 may include multiple supply tanks or containers such that when one tank is emptied, another tank may replace the empty tank without disrupting service.

As shown, process 1000 may include monitoring (at 1010) supply level. Supply level may be monitored using a fluid sensor or other appropriate sensor.

Process 1000 may include determining (at 1020) whether the minimum supply threshold has been met or exceeded by comparing the supply level measured (at 1020) to a specified threshold. If the supply level is determined (at 1020) to be below the minimum threshold, the process may include advancing (at 1030) to the next available supply container or tank. Such multiple tanks may be arranged in a "ping-pong" configuration whereby when a first tank is emptied, a second tank is utilized, allowing the first tank to be replaced or refilled without disruption in service. Some embodiments of SDTS 100 may include a magazine of multiple tanks that may allow additional cycles of tank replacement before maintenance is required.

As shown, process 1000 may include verifying (at 1040) the new supply. Such verification may include, for instance, scanning a tag (e.g., an RFID tag) or graphic code associated with the tank or container. In some embodiments, a tester device may be utilized to confirm the presence of an inert synthetic agent. Verification may further include verification of proper operating conditions or other evaluation criteria. For instance, tank temperature may be measured to determine if the temperature is within a specified range.

Process 1000 may include determining (at 1050) whether the supply is valid. Such a determination may be made by evaluating scanned or sensed information to determine whether the supply is valid. Such information may include information embedded in a graphic code, information associated with an RFID tag, detection of an inert synthetic agent, and/or other appropriate criteria.

The process may include rejecting (at 1060) the supply if the process determines (at 1050) that the supply is not valid. Rejection may include disabling use of SDTS 100 or otherwise preventing distribution of unknown materials (e.g., by evaluating a next tank, if available).

As shown, process 1000 may include sending (at 1070) a status update. Such an update may include a message sent to various other system resources, such as a server or user device. The type or other attributes of the status update may be based on the supply level, supply validity, and/or other relevant factors. For instance, if a minimum supply threshold is determined (at 1020) to have been met, the process may send a status notification to a server indicating the supply level. As another example, if the supply is rejected (at 1060) and no other tanks are available, the process may send a notification to a technician indicating that maintenance is required.

Figure 11:
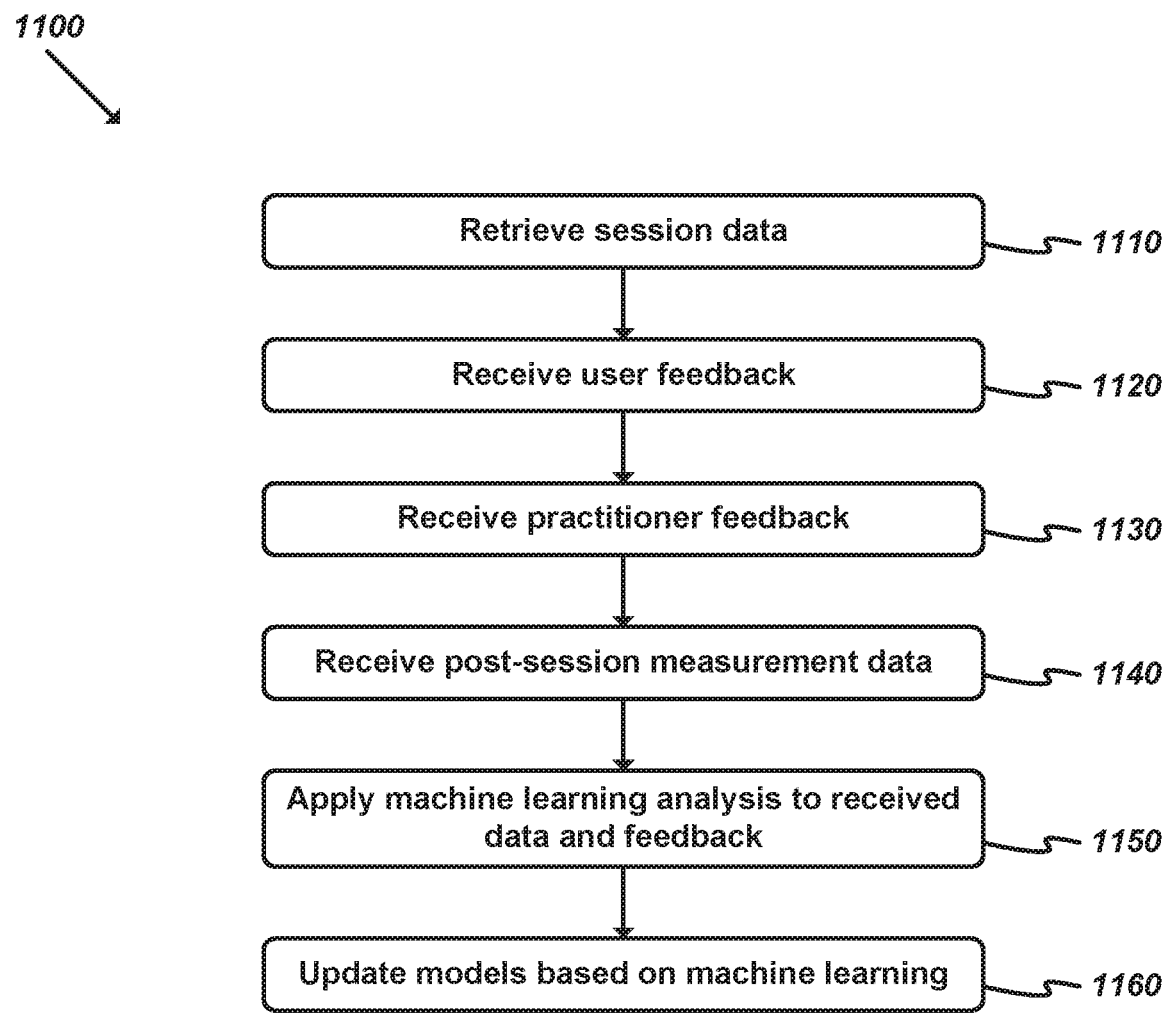
FIG. 11 illustrates a flow chart of an exemplary process that applies machine learning to virtual telemedicine services.

FIG. 11 illustrates an example process 1100 for applying machine learning to virtual telemedicine services. Such a process may be used to update recommendation models, condition profiles, user profiles, and/or other appropriate elements associated with SDTS 100 or use thereof. The process may be performed whenever new data becomes available, at regular intervals, and/or under other appropriate conditions. In some embodiments, process 1100 may be performed by SDTS 100.

As shown, process 1100 may include retrieving (at 1110) session data. Such data may include data associated with disinfections, access control, telemedicine sessions, and/or any other user interactions with SDTS 100. Session data may be retrieved from a local storage and/or various remote storages. Session data may include data associated with multiple users and/or SDTSs 100. Session data may be filtered or processed in various appropriate ways, based on various appropriate attributes (e.g., user attributes such as age or gender, SDTS 100 attributes such as calibration date or location, etc.).

The process may include receiving (at 1120) user feedback. Such feedback may be received directly (e.g., via follow-up survey) and/or indirectly (e.g., measured biometric data may be analyzed to determine whether a recommendation was effective or an identification of a condition was accurate).

Process 1100 may include receiving (at 1130) practitioner feedback. Such practitioner feedback may be received directly (e.g., a survey of practitioners may indicate that blood oxygen level should be measure before every consultation) and/or indirectly (e.g., requests for additional data from practitioners during telemedicine sessions may be analyzed to determine that requests for blood oxygen level data are made in a large percentage of sessions).

The process may include receiving (at 1140) post-session measurement data. Such data may include, for instance, biometric data collected during later user interactions with an SDTS 100. For instance, an employee-user may be determined to be suffering from a fever and fever-reducing medications may be recommended. Post-session measurement data my include temperature measurements of the employee within some time limit of the recommendation of fever-reducing medication (e.g., temperature data for the next three days).

As shown, process 1100 may include applying (at 1150) machine learning analysis to the received data and feedback. Such application of machine learning may include generating or updating various selection models or algorithms utilized by SDTS 100. For instance, if a specific fever-reducing medication is associated with faster recovery, medication selection algorithms may be updated to be more likely to select and recommend the specific fever-reducing medication.

The process may include updating (at 1160) various models based on the machine learning. Such updates may include updates to selection models or algorithms, identification models or algorithms, treatment models or algorithms, and/or other appropriate models or algorithms.

One of ordinary skill in the art will recognize that processes 600-1100 may be implemented in various different ways without departing from the scope of the disclosure. For instance, the elements may be implemented in a different order than shown. As another example, some embodiments may include additional elements or omit various listed elements. Elements or sets of elements may be performed iteratively and/or based on satisfaction of some performance criteria. Non-dependent elements may be performed in parallel. In addition, various different devices or components may implement processes 600-1100 than those described above. For instance, telemedicine server 520, user device 510, and/or practitioner device 540 may perform some or all of processes 600-1100.

The processes and modules described above may be at least partially implemented as software processes that may be specified as one or more sets of instructions recorded on a non-transitory storage medium. These instructions may be executed by one or more computational element(s) (e.g., microprocessors, microcontrollers, digital signal processors (DSPs), application-specific integrated circuits (ASICs), field programmable gate arrays (FPGAs), other processors, etc.) that may be included in various appropriate devices in order to perform actions specified by the instructions.

As used herein, the terms "computer-readable medium" and "non-transitory storage medium" are entirely restricted to tangible, physical objects that store information in a form that is readable by electronic devices.

Figure 12:
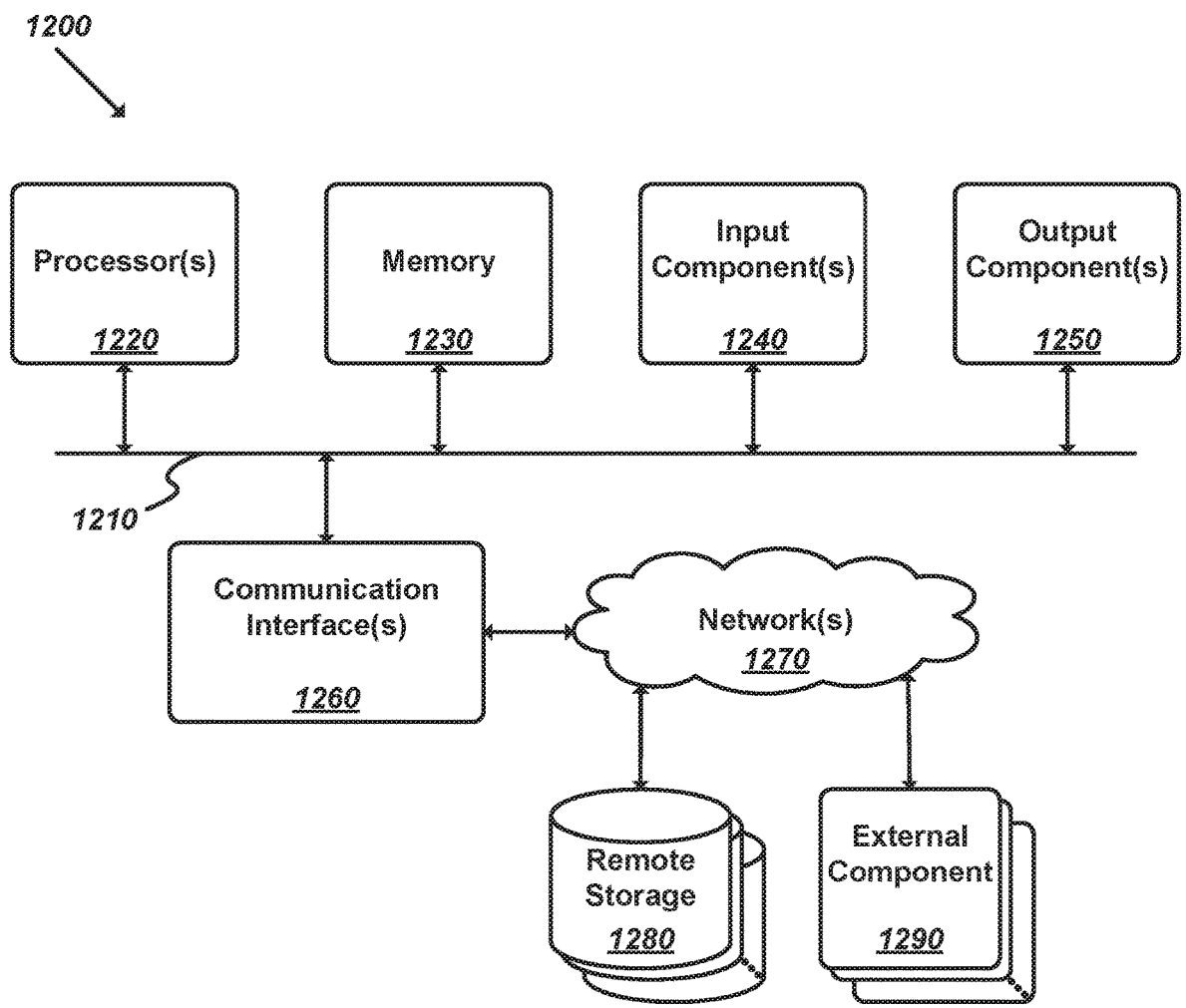
FIG. 12 illustrates a schematic block diagram of one or more exemplary devices used to implement various embodiments.

FIG. 12 illustrates a schematic block diagram of an exemplary device (or system or devices) 1200 used to implement some embodiments. For example, the system described above in reference to FIG. 5 may be at least partially implemented using device 1200. As another example, the devices described above in reference to FIG. 1A, FIG. 1B, FIG. 2, FIG. 3, and FIG. 4 may be at least partially implemented using device 1200. As still another example, the processes described in reference to FIG. 6, FIG. 7, FIG. 8, FIG. 9, FIG. 10, and FIG. 11 may be at least partially implemented using device 1200.

Device 1200 may be implemented using various appropriate elements and/or sub-devices. For instance, device 1200 may be implemented using one or more personal computers (PCs), servers, mobile devices (e.g., smartphones), tablet devices, wearable devices, and/or any other appropriate devices. The various devices may work alone (e.g., device 1200 may be implemented as a single smartphone) or in conjunction (e.g., some components of the device 1200 may be provided by a mobile device while other components are provided by a server).

As shown, device 1200 may include at least one communication bus 1210, one or more processors 1220, memory 1230, input components 1240, output components 1250, and one or more communication interfaces 1260.

Bus 1210 may include various communication pathways that allow communication among the components of device 1200. Processor 1220 may include a processor, microprocessor, microcontroller, digital signal processor, logic circuitry, and/or other appropriate processing components that may be able to interpret and execute instructions and/or otherwise manipulate data. Memory 1230 may include dynamic and/or non-volatile memory structures and/or devices that may store data and/or instructions for use by other components of device 1200. Such a memory device 1230 may include space within a single physical memory device or spread across multiple physical memory devices.

Input components 1240 may include elements that allow a user to communicate information to the computer system and/or manipulate various operations of the system. The input components may include keyboards, cursor control devices, audio input devices and/or video input devices, touchscreens, motion sensors, etc. Output components 1250 may include displays, touchscreens, audio elements such as speakers, indicators such as light-emitting diodes (LEDs), printers, haptic or other sensory elements, etc. Some or all of the input and/or output components may be wirelessly or optically connected to the device 1200.

Device 1200 may include one or more communication interfaces 1260 that are able to connect to one or more networks 1270 or other communication pathways. For example, device 1200 may be coupled to a web server on the Internet such that a web browser executing on device 1200 may interact with the web server as a user interacts with an interface that operates in the web browser. Device 1200 may be able to access one or more remote storages 1280 and one or more external components 1290 through the communication interface 1260 and network 1270. The communication interface(s) 1260 may include one or more application programming interfaces (APIs) that may allow the device 1200 to access remote systems and/or storages and also may allow remote systems and/or storages to access device 1200 (or elements thereof).

It should be recognized by one of ordinary skill in the art that any or all of the components of computer system 1200 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

Device 1200 may perform various operations in response to processor 1220 executing software instructions stored in a computer-readable medium, such as memory 1230. Such operations may include manipulations of the output components 1250 (e.g., display of information, haptic feedback, audio outputs, etc.), communication interface 1260 (e.g., establishing a communication channel with another device or component, sending and/or receiving sets of messages, etc.), and/or other components of device 1200.

The software instructions may be read into memory 1230 from another computer-readable medium or from another device. The software instructions stored in memory 1230 may cause processor 1220 to perform processes described herein. Alternatively, hardwired circuitry and/or dedicated components (e.g., logic circuitry, ASICs, FPGAs, etc.) may be used in place of or in combination with software instructions to implement processes described herein. Thus, implementations described herein are not limited to any specific combination of hardware circuitry and software.

The actual software code or specialized control hardware used to implement an embodiment is not limiting of the embodiment. Thus, the operation and behavior of the embodiment has been described without reference to the specific software code, it being understood that software and control hardware may be implemented based on the description herein.

While certain connections or devices are shown, in practice additional, fewer, or different connections or devices may be used. Furthermore, while various devices and networks are shown separately, in practice the functionality of multiple devices may be provided by a single device or the functionality of one device may be provided by multiple devices. In addition, multiple instantiations of the illustrated networks may be included in a single network, or a particular network may include multiple networks. While some devices are shown as communicating with a network, some such devices may be incorporated, in whole or in part, as a part of the network.

Some implementations are described herein in conjunction with thresholds. To the extent that the term "greater than" (or similar terms) is used herein to describe a relationship of a value to a threshold, it is to be understood that the term "greater than or equal to" (or similar terms) could be similarly contemplated, even if not explicitly stated. Similarly, to the extent that the term "less than" (or similar terms) is used herein to describe a relationship of a value to a threshold, it is to be understood that the term "less than or equal to" (or similar terms) could be similarly contemplated, even if not explicitly stated. Further, the term "satisfying," when used in relation to a threshold, may refer to "being greater than a threshold," "being greater than or equal to a threshold," "being less than a threshold," "being less than or equal to a threshold," or other similar terms, depending on the appropriate context.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items and may be used interchangeably with the phrase "one or more." Where only one item is intended, the terms "one," "single," "only," or similar language is used. Further, the phrase "based on" is intended to mean "based, at least in part, on" unless explicitly stated otherwise.

The foregoing relates to illustrative details of exemplary embodiments and modifications may be made without departing from the scope of the disclosure. Even though particular combinations of features are recited in the claims and/or disclosed in the specification, these combinations are not intended to limit the possible implementations of the disclosure. In fact, many of these features may be combined in ways not specifically recited in the claims and/or disclosed in the specification. For instance, although each dependent claim listed below may directly depend on only one other claim, the disclosure of the possible implementations includes each dependent claim in combination with every other claim in the claim set.

We claim:

1. A device comprising:
   an inner wall comprising a proximate side wall portion, a distal side wall portion, and a ceiling;
   a floor, wherein a disinfecting area of the device is enclosed by the inner wall and the floor;
   one or more motion detection sensors that detect a person within the disinfecting area of the device;
   a biometric sensor that collects at least one measurement associated with the detected person, the at least one measurement including body temperature;
   a dispenser that distributes sanitizing solution from the ceiling by converting a liquid sanitizing solution to a mist and distributing the mist throughout the disinfecting area when a person is detected within the disinfecting area; and
   an exhaust fan that further distributes the mist throughout the disinfecting area and prevents the mist from escaping the disinfecting area by collecting the mist at the floor.

2. The device of claim 1 further comprising at least one user interface element that provides an indication that disinfection is complete.

3. The device of claim 1 further comprising an access controller associated with an access gate, wherein the access controller opens the access gate when the body temperature is below a specified threshold.

4. The device of claim 1 further comprising at least one camera that captures user identifying information, wherein the user identifying information is associated with a stored user profile, wherein the stored user profile comprises at least one previously-collected measurement.

5. The device of claim 1 further comprising a two-way communication interface that communicates with at least one practitioner device.

6. The device of claim 5, wherein the two-way communication interface comprises a touchscreen.

7. The device of claim 1, wherein the disinfecting area comprises an entrance and an exit allowing users to pass through the disinfecting area.

* * * * *